United States Patent [19]

Siegrist et al.

[11] 3,991,049
[45] Nov. 9, 1976

[54] AROMATIC COMPOUNDS CONTAINING ETHYLENE DOUBLE BONDS, PROCESSES FOR THEIR MANUFACTURE AND USE

[75] Inventors: Adolf Emil Siegrist, Basel; Peter Liechti, Binningen; Hans Rudolf Meyer; Kurt Weber, both of Basel, all of Switzerland

[73] Assignee: Ciba-Geigy AG, Basel, Switzerland

[22] Filed: Sept. 16, 1974

[21] Appl. No.: 506,663

Related U.S. Application Data

[63] Continuation of Ser. No. 292,229, Sept. 25, 1972, abandoned, which is a continuation of Ser. No. 743,001, July 8, 1968, abandoned.

[30] Foreign Application Priority Data
July 14, 1967  Switzerland.................. 101110/67

[52] U.S. Cl. ................. 260/240 D; 260/240 R; 260/240 CA; 260/611 A; 260/612 R; 260/613 D; 260/649 R; 260/649 DP; 260/668 PY; 260/669 R; 260/668 R; 260/668 C; 260/668 F; 252/301.22; 252/301.35
[51] Int. Cl.² ............. C07D 333/08; C07C 25/18
[58] Field of Search ... 260/240 CA, 649 R, 649 DP, 260/668 C, 240 R, 240 D, 649 DD

[56] References Cited
UNITED STATES PATENTS 3,177,153  4/1965  Pommer et al................ 260/649 R
3,177,208  4/1965  Stilz et al...................... 260/240
3,825,534  7/1974  Weber........................... 260/649 DP

*Primary Examiner*—Arthur P. Demers
*Attorney, Agent, or Firm*—Joseph G. Kolodny; Edward McC. Roberts; Prabodh I. Almaula

[57] ABSTRACT

The invention provides a new process for the manufacture of aromatic compounds which at least once contain a benzene ring of an aromatic carbocyclic ring system bonded by an ethylene double bond in conjugation with a further aromatic ring system, i.e. contain the stilbene skeleton or stilbene analogon as central structural element, as well as certain classes of new compounds of this type. The process is characterized by the reaction of a Schiff base of an aromatic aldehyde with an aromatic carbocyclic six-membered ring compound which contains one to four methyl groups bonded to ring carbon atoms of a benzene ring, which furthermore contains aromatic rings which are exclusively six-membered carbocyclic rings, and wherein those benzene rings whose methyl groups are to be caused to react are free of other substituents which contain atoms which are replaceable by alkali metal. The reaction is carried out in the presence of (a) a strongly basic alkali compound and (b) an N-dialkylacylamide as solvent. The compounds obtainable according to this process show a marked fluorescence emission and therefore are suitable for all purposes where fluorescence properties are used, as for instance optical brighteners, scintillators fluorescence dyes, etc.

19 Claims, No Drawings

AROMATIC COMPOUNDS CONTAINING ETHYLENE DOUBLE BONDS, PROCESSES FOR THEIR MANUFACTURE AND USE

This is a continuation of application Ser. No. 292,229, filed on Sept. 25, 1972, now abandoned which is a continuation of application Ser. No. 743,001 filed on July 8, 1968, now abandoned.

The present invention comprises a new and chemically peculiar process for the manufacture of aromatic compounds, which contain, at least once, a benzene ring of an aromatic carbocyclic ring system bonded by an ethylene double bond in conjugation with a further aromatic ring system, the new substances which have become accessible by this process, as well as the use of these substances as optical brighteners.

The process according to the invention is characterised in that (A) a Schiff base of an aromatic aldehyde is reacted with (B) methyl groups of a compound, containing at least one aromatic carbocyclic 6-membered ring, which (1) contains one to four methyl groups bonded to ring carbon atoms of a benzene ring and (2) exclusively contains 6-membered carbocyclic aromatic rings, wherein (3) those benzene rings of which the methyl groups are to be reacted must be free of other substituents containing atoms replaceable by alkali metal, and (4) this aromatic compound containing carbocyclic 6-membered rings either consists (a) of a benzene ring or (b) of a condensed benzene ring system containing linearly or angularly annellated benzene rings or (c) of several benzene rings or condensed benzene ring systems linked together by C—C single bonds, or (d) represents an arrangement of several benzene rings or condensed ring systems which contains at least one linkage by an unsaturated carbon atom chain having 2 or 4 carbon atoms which permits a continuous conjugation from ring to ring, with this reaction being carried out in the presence of a strongly basic alkali compound and with an acylamide of formula $$[(Alkyl)_2 N]_w\text{—Acyl} \qquad (1)$$

being used as the reaction medium, with the term "Alkyl" representing a lower alkyl group, the term "Acyl" representing the residue of a lower aliphatic carboxylic acid or of phosphoric acid and w representing the basicity of the acid, and wherein, in the case of alkali hydroxides being used as the strongly basic alkali compound, these alkali hydroxides being permitted to have a water content of up to 25%.

Within the framework of these conditions, the use of a strongly basic potassium compound as the strongly basic alkali compound and the use of an anil of an aromatic aldehyde, containing 1 to 4 rings with 5 to 6 ring members, as the Schiff base is of interest for practical purposes.

As can be seen, the process of the invention defined above is capable of very broad application provided the basic prerequisites mentioned are fulfilled. This is particularly true with regard to possibilities of substitution, for which in principle the only requirement made — arising from the above definition — is that those benzene rings whose methyl groups are to be reacted must be free of other substituents which contain hydrogen atoms replaceable by alkali metal, such as for example hydroxyl groups, carboxylic acid groups or sulphonic acid groups. This means that the methyl groups to be reacted according to the process of the invention should be capable of carbanion formation in the presence of alkali metal cations. "Competitive reactions" of the alkali metal cations with other substituents, such as for example salt formation, must not occur.

The synthesis characterised above is particularly valuable when applied to the reaction of the following basic types of starting materials:

I. The reaction of compounds of formula

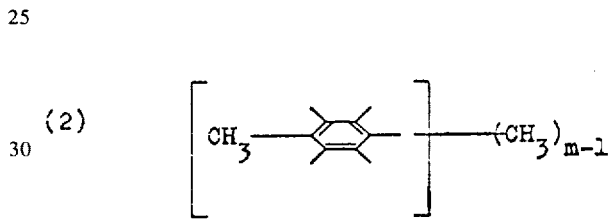

(2)

wherein $m$ denotes an integer from 1 to 4 and the free valencies of the formula, to the extent that they do not carry any methyl groups, can be occupied by a hydrogen atom or substituent of the 1st. order which are free of atoms replaceable by alkali metal, especially hydrogen atoms.

II. The reaction of diphenyl compounds of formula

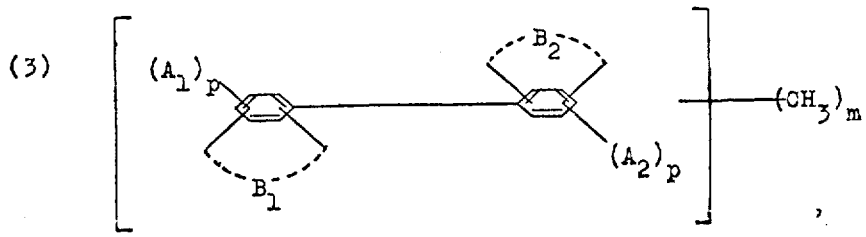

(3)

wherein the symbols $A_1$ and $A_2$ denote hydrogen or a phenyl or diphenyl residue and the symbols $B_1$ and $B_2$ are intended to represent that each of the two phenyl groups of the diphenyl skeleton can contain further linearly or angularly annellated benzene rings, $p$ represents an integer from 1 to 3 and $m$ denotes an integer from 1 to 4, wherein (a) the methyl groups indicated in the formula must be bonded to ring carbon atoms of the benzene rings of the formula, and (b) the benzene rings carrying methyl groups must be free of substituents of the 2nd. order and of such substituents of the 1st. order as contain atoms replaceable by alkali metal.

III. The reaction of naphthyl compounds of formula

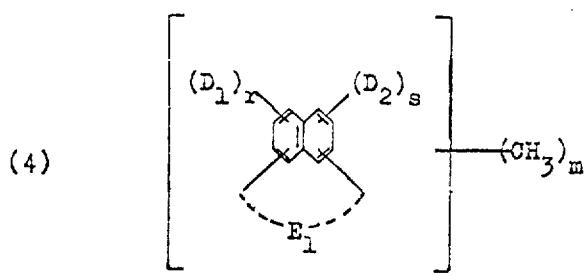

(4)

wherein the symbols $D_1$ and $D_2$ represent hydrogen or a phenyl or diphenyl residue and the symbol $E_1$ denotes that further linearly or angularly annellated benzene rings, which in turn may carry phenyl or diphenyl residues, may be condensed onto each of the rings of the naphthyl nucleus, r and s represent the numbers 1 to 4 to the extent that positions are still available, m denotes an integer from 1 to 4, and at least one methyl group is bonded to a ring carbon atom of the naphthyl nucleus of the formula, and the benzene rings carrying methyl groups should be free of substituents of the 2nd. order and of such substituents of the 1st. order as contain atoms replaceable by alkali metal.

IV. The reaction of aromatic compounds of formula (5) 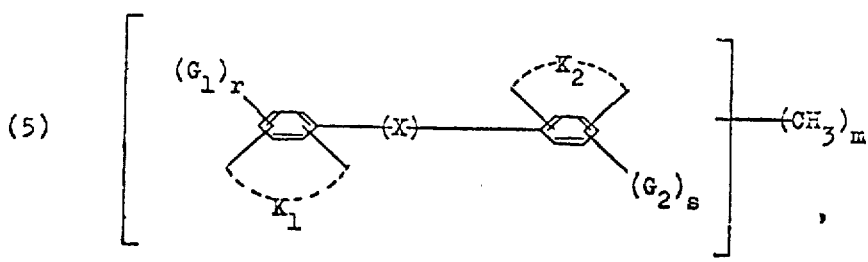

wherein X denotes a bridge member of the series —CH=CH—, —CH=CH—CH=CH—, —C≡C—, the symbols $G_1$ and $G_2$ represent hydrogen atoms or phenyl groups, r and s represent an integer from 1 to 3, and the symbols $K_1$ and $K_2$ are intended to represent that each of the two phenyl groups of the formula may contain further linearly or angularly annellated benzene rings, m denotes an integer from 1 to 4, and at least one methyl group is intended to be bonded to a ring carbon atom of a phenyl residue of the above formula skeleton, and wherein the benzene rings carrying methyl groups should be free of substituents of the 2nd. order and of such substituents of the 1st. order as contain atoms replaceable by alkali metal.

In the above formulae, 3, 4 and 5 the symbols B, E and K are intended to express that at this point condensed benzene ring systems may be present in an arrangement which is in itself known, to the extent that the corresponding positions are free. Thus for example the symbol $E_1$ is intended to express that further benzene ring systems, (such as for example the benzene nucleus itself, the naphthalene ring system and the like) can in principle be condensed onto all positions of the naphthalene basic skeleton of formula (3), that is to say both to either of the two rings and also to both rings simultaneously. The methyl groups may herein themselves be present at any desired position of any benzene ring of the formula, and preferably at least one methyl group is present at one of the benzene nuclei directly drawn in the structural formula. It is also possible for several methyl groups to be present, and to be made to react in the sense according to the invention, at one and the same benzene nucleus.

Within the framework of the above main types of possible reactions, the use of the subgroups of compounds listed below — always following the reaction principle given above — is of particular interest:

V. The reaction of compounds of formula (6) 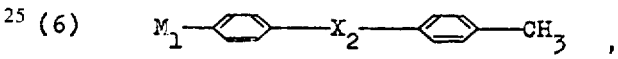

wherein $X_2$ denotes a bridge member of the series —CH=CH—, —CH=CH—CH=CH—, —C≡C—C≡C—, —C≡C—, and $M_1$ represents hydrogen of the methyl group.

VI. The reaction of an anil of an aromatic aldehyde containing 1 to 2 five-membered to six-membered rings, with a methylbenzene compound of formula (7) 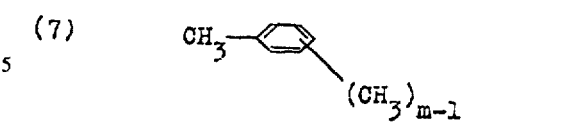

wherein m in this formula represents a number from 1 to 4. The benzene nucleus should herein be free of substituents of the 2nd. order but may contain such substituents of the 1st. order as are free of atoms which are replaceable by alkali metal.

VII. The reaction of an anil of an aromatic aldehyde containing 1 to 2 five-membered to six-membered rings with a diphenyl compound of formula (8) 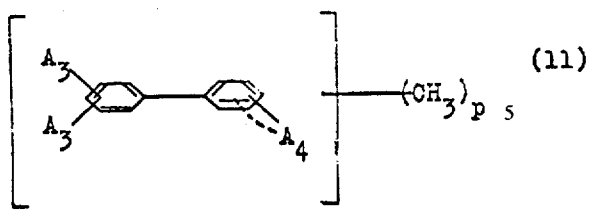 (11) 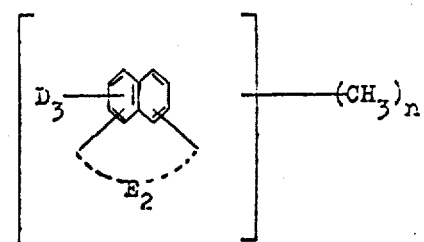

wherein, in this formula, $A_3$ represents a hydrogen atom, a phenyl group or a diphenyl group, $A_4$ represents a hydrogen atom, a phenyl group or a condensed-on benzene ring and $p$ represents an integer from 1 to 3, and at least one methyl group is bonded to a phenyl residue of the diphenyl nucleus. Herein, the benzene rings carrying methyl groups should be free of substituents of the 2nd. order and of such substituents of the 1st. order as contain atoms replaceable by alkali metal, whilst the nuclei which are free of methyl groups may contain substituents of the 1st. order.

VIII. The reaction of a compound of formula (9) 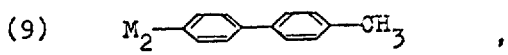

wherein $M_2$ represents hydrogen, the methyl group or phenyl.

IX. The reaction of a compound of formula

(10) 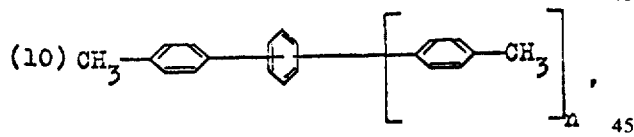

wherein $n$ represents the numbers 1 or 2.

X. The reaction of an anil of an aromatic aldehyde containing 1 to 2 five-membered to six-membered rings, with a naphthyl compound of formula wherein the symbol $E_2$ denotes that the naphthalene ring of this formula is present either as such or contains, at positions 1, 2, 3, 4, 5 and 8, 1 to 2 further condensed-on benzene nuclei in the arrangement of condensed polynuclear aromatic carbocyclic six-membered ring systems which are in themselves known, and the symbol $D_3$ represent a phenyl residue present in positions 6, 7 or, were available, in positions 5 or 8, $n$ denotes an integer from 1 to 3 and at least one methyl group is bonded to the naphthalene nucleus. Herein the benzene rings carrying methyl groups should be free of substituents of the 2nd. order and of such substituents of the 1st. order as contain atoms replaceable by alkali metal, whilst the nuclei which are free of methyl groups may contain substituents of the 1st. order.

XI. The reaction of a compound of formula

(12) 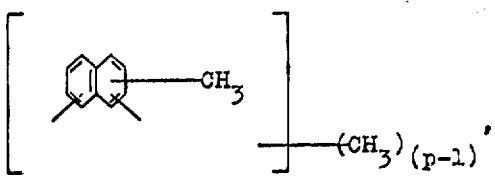

wherein $p$ represents an integer from 1 to 3.

XII. The reaction of an anil of an aromatic aldehyde containing 1 to 2 five-membered to six-membered rings, with an aromatic compound of formula

(13) 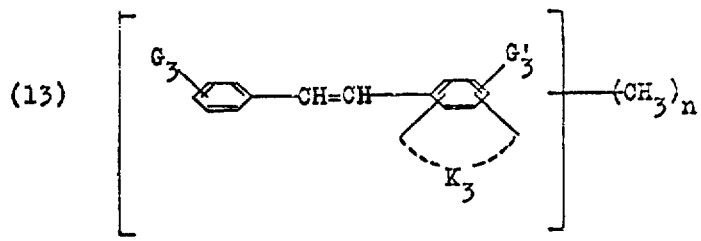

wherein the symbol $K_3$ denotes that two adjacent positions of the phenyl residue which carries $K_3$ are occupied by hydrogen atoms or contain a condensed-on benzene residue, and $G_3$ and $G_3'$ represent hydrogen or a phenyl residue, whilst $n$ represents an integer from 1 to 2 and at least one methyl group is bonded to a phenyl residue of the stilbene skeleton, and wherein the benzene rings carrying methyl groups should be free of substituents of the 2nd. order and of such substituents of the 1st. order as contain atoms replaceable by alkali metal, and the nuclei which are free of methyl groups may contain substituents of the 1st. order.

XIII. The reaction of compounds of formula

(14) 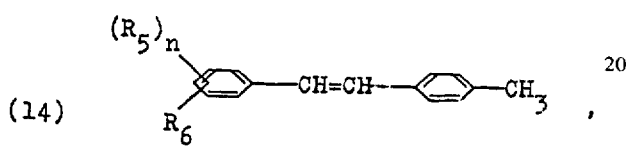

wherein $R_5$ represents hydrogen or an alkoxy group having 1 to 4 carbon atoms and $R_6$ represents hydrogen, an alkoxy group with 1 to 4 carbon atoms or a phenyl group, and $n$ denotes the numbers 1 or 2.

XIV. The reaction of anils of aldehydes of the benzene series with compounds of formula

(15) 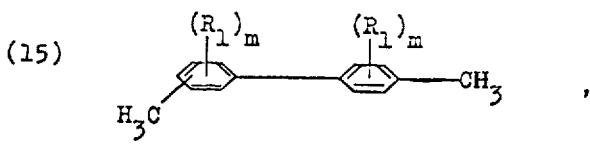

wherein $R_1$ represents hydrogen or other substituents of the 1st. order which are free of atoms which are replaceable by alkali metal, and $m$ represents an integer from 1 to 4.

XV. The reaction of anils of aldehydes of the benzene series with compounds of formula

(16) 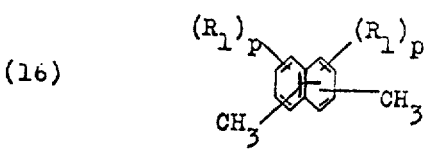

wherein the methyl groups are preferably in positions 2 and 6, $R_1$ represents hydrogen atoms or other substituents of the 1st. order which are free of atoms which are replaceable by alkali metal, and $p$ represents an integer from 1 to 3.

XVI. The reaction of anils of aldehydes of the benzene series with compounds of formula

(17) 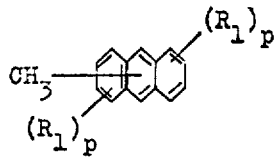

wherein the methyl group may be in positions 1, 2 or 9, $R_1$ represents a hydrogen atom or other substituents of the 1st. order which are free of atoms which are replaceable by alkali metal, and $p$ represents an integer from 1 to 3.

XVII. The reaction of compounds of formula

(18) 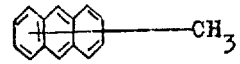

wherein the methyl group may occupy any desired position in the anthracene ring system.

XVIII. The reaction of anils of aldehydes of the benzene series with compounds of formula

(19) 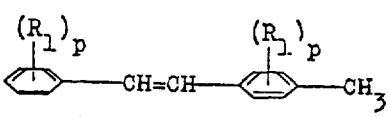

wherein $R_1$ represents hydrogen or other substituents of the 1st. order which are free of atoms which are replaceable by alkali metal and $p$ represents an integer from 1 to 3.

In the abovementioned formulae 16 and 17 the entry of a methyl group or of the residue $R_1$ extending across two rings denotes that these substituents may be present on both of these rings.

As regards the substitution possibilities in the case of compounds according to formulae 7, 8, 11, 13, 15, 16, 17 and 19 it should be explained that the following predominantly require consideration as substituents of the 1st. order: halogens such as fluorine, chlorine or bromine, alkyl groups having more than 2 carbon atoms but mostly not containing more than 18 carbon atoms and preferably up to 12 carbon atoms, which are optionally of branched nature, cycloalkyl groups such as cyclohexyl, alkoxy groups having 1 to 18, preferably 1 to 6, carbon atoms as well as their sulphur analogues (alkylmercapto groups), dialkylamino groups preferably having higher alkyl groups, aryloxy (especially phenyloxy) groups as well as phenylmercapto groups.

In addition to this group of substituents of predominant interest further substituents which meet the requirements posed above may of course also be present, such as for example the trifluoromethyl group, the methylenedioxy group and the like.

The derivatives containing 1 to 4 methyl groups of the following hydrocarbons may be quoted as examples of the ring systems defined by the above formulae, the specification of possible substituents being dispensed with: Type according to formula (3):

(20a) 

(20b) 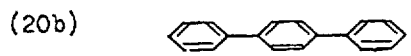

(20c) 

(20d) 

(20e) 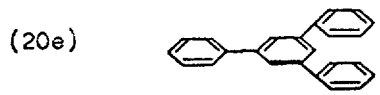

(20f) 

(20g) 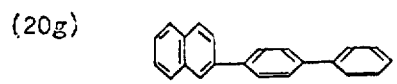

Type according to formula (4):

(21a) 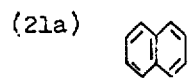   (21b) 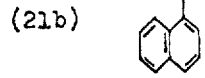   (21c) 

(21d) 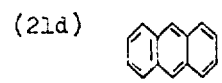   (21e) 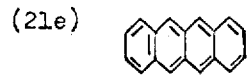   (21f) 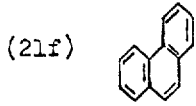

(21g) 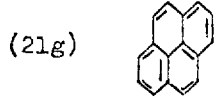

Type according to formula (5)

(22a) 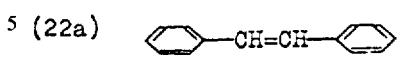

(22b) 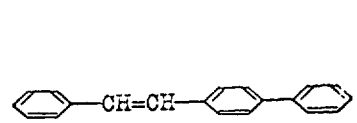

(22c) 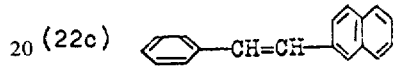

(22d) 

(22e) 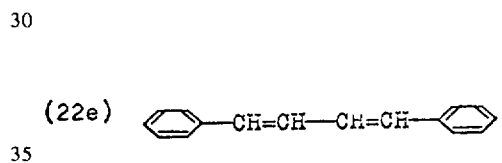

(22f) 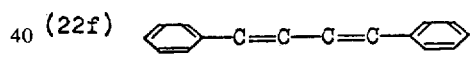

The following may for example be mentioned as methylbenzenes of the type according to formula (2)

(23a) 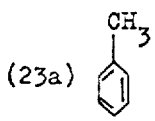

(23b) 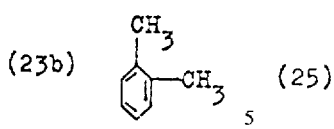

(25) 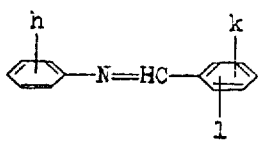

(23c) 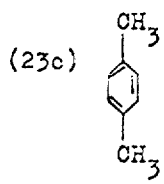

(23d) 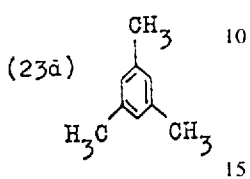

wherein k and l may be identical or different and denote hydrogen atoms, chlorine atoms or methoxy groups and h represents chlorine or preferably hydrogen. Adjacent k and l may together also form an O—CH$_2$—O— group. Another important variant of aromatic anils corresponds to the formula (23e) 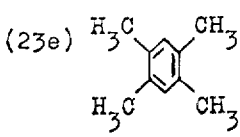

(23f) 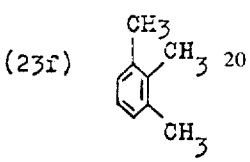

(26) 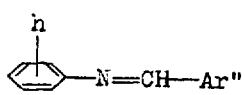

wherein h (as above) represents a hydrogen atom or chlorine and Ar" denotes a naphthyl or diphenyl residue.

The present process is of particular importance in the case where an aromatic aldehyde-anil of formula

(27) 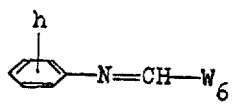

(23g) 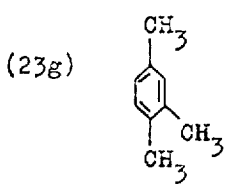

(23h) 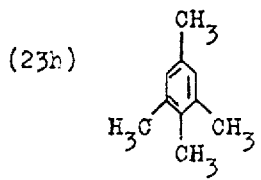

is used as the Schiff base, wherein h represents hydrogen or halogen and W$_6$ represents phenyl, α-naphthyl, β-naphthyl, diphenyl-4, thienyl-2, pyridyl-3, (methylenedioxy-3,4)-phenyl or a phenyl residue (27a) 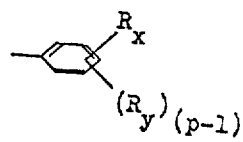

The Schiff base to be used as the 2nd. reagent in the present process must — as will be obvious — be free of reactive methyl groups, for example of methyl groups in the p-position to the azomethine grouping. The possible Schiff bases in turn represent the (known) condensation products of aldehydes of aromatic character with primary amines (of aliphatic, aromatic or heterocyclic nature) of which the amino group is bonded to a tertiary carbon atom. Compounds of this nature can accordingly be written as azomethine compounds of formula

(24) Ar—CH=N—C(tertiary)≦ wherein Ar denotes an aromatic residue. Herein either one or both of the components (aldehyde and amine) required for the synthesis of the Schiff bases may contain further substituents, provided the above restriction is observed. Since the amine residue, especially the aniline residue, is split off during the reaction and is no longer present in the final product the presence of substituents is here generally not indicated and is of no interest. Nevertheless substituents which do not interfere with the reaction, or hinder it, for example chlorine atoms, may be present in this ring also. The benzene residue bonded to the =HC— group may for example carry halogen atoms such as bromine or chlorine or alkoxy groups such as methoxy or ethoxy. Schiff bases of preferred interest are those of aromatic aldehydes with anilines, that is to say aromatic aldehydeanils. Such anils for example correspond to the formula wherein R$_x$ denotes halogen, an alkyl group containing 2 to 4 carbon atoms, a phenoxy group or an alkoxy group containing 1 to 4 carbon atoms, R$_y$ represents an alkoxy group containing 1 to 4 carbon atoms and p represents the numbers 1 to 3.

The reaction of aldehyde-anils according to formula (27) with compounds according to formulae (6), (7), (9), (10), (12), (14) and (18) has proved of particular interest for practical purposes.

The following may for example be mentioned as suitable mono-aldehydes for the synthesis of the Schiff bases: aldehydes of the benzene series such as benzaldehyde or its halogenated analogues such as the monochloro and dichloro analogues, hydroxybenzaldehydes such as p-methoxybenzaldehyde, p-phenoxybenzaldehyde, alkylated benzaldehydes to the extent that they do not contain any p-methyl groups, such as toluylaldehyde, xylyl-aldehyde or cumoyl-aldehyde, methylenedioxybenzaldehyde (piperonal), 4-dimethylamino-benzaldehyde, 4-diethylamino-benzaldehyde, diphenyl-aldehyde; aldehydes of the naphthalene series such as α-naphthaldehyde and β-naphthaldehyde, and heterocyclic aldehydes such as for example furfurol, thiophene-2-aldehyde and pyridine-3-aldehyde.

As suitable amines there may for example be mentioned the anilines, naphthylamines or, as an aliphatic representative, tert.butylamine.

The compounds of formulae (2) to (19) may inherently be reacted with the aldehyde-anils in the presence of any desired strongly polar neutral to alkaline organic solvent which is free of atoms, especially hydrogen atoms, which are replaceable by alkali metals. In practice however one considers, as such solvents, above all di-alkylated acylamides of the type

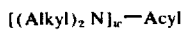 (1)

wherein "Alkyl" denotes a lower alkyl group (containing 1 to 4 carbon atoms), especially a methyl group, "Acyl" denotes the residue of a lower carboxylic acid (containing 1 to 4 carbon atoms), especially formic acid or acetic acid, or phosphoric acid, and $w$ indicates the basicity of the acid. As important representatives of such solvents there may be mentioned: dimethylformamide, diethylformamide, dimethylacetamide and hexamethyl-phosphoric acid triamide. It is also possible to consider solvent mixtures.

A strongly basic alkali compound is furthermore required for the reaction. By strongly basic alkali compounds there are to be understood, within the framework of the present invention, such compounds of the alkali metals (main group I of the periodic table of the elements) including ammonium as exhibit a basic strength of at least approximately that of lithium hydroxide. Accordingly, they may be compounds of lithium, sodium, potassium, rubidium, caesium or ammonium of the type of, for example, the alcoholates, hydroxides, amides, hydrides or sulphides, or strongly basic ion exchangers. It is advantageous (above all if mild reaction condition as regards reaction temperature appear indicated) to use potassium compounds of the composition

(28) $KOC_{x-1}H_{2x-1}$ wherein $x$ represents an integer from 1 to 6, such as for example potassium hydroxide or potassium tertiary-butylate. In the case of alkali alcoholates and alkali amides (and hydrides) it is, herein, necessary to work in a practically anhydrous medium, whilst in the case of alkali hydroxides water contents of up to 25% (for example crystal water contents) are permitted. In the case of potassium hydroxide a water content of up to about 15% has proved appropriate. Sodium methylate, sodium hydroxide, sodium amide, lithium amide, lithium hydroxide, rubidium hydroxide, caesium hydroxide and the like may be mentioned as examples of other usable alkali compounds. It is of course possible to work with mixtures of such bases.

According to the preceding explanations, a practically important embodiment of the present invention consists of reacting anils of aldehydes of the benzene and naphthalene series with compounds of formulae (2), (3), (4) and (5), with this reaction being carried out in the presence of an alkali compound having a basic strength at least equal to that of lithium hydroxide, preferably potassium tertiary-butylate or potassium hydroxide, in a solvent which corresponds to the formula

 (1)

wherein "Alkyl" denotes a lower alkyl group, "Acyl" denotes the residue of a lower aliphatic carboxylic acid or phosphoric acid and $w$ denotes the basicity of the acid, preferably in dimethylformamide.

The compounds of formula (2) to (5) are appropriately reacted with the aldehyde-anils in equivalent quantities so that neither component is present in a significant excess. Where several methyl groups are to be reacted, an excess of aldehyde-anil can be of advantage. It is advantageous to use at least the equivalent quantity of the alkali compound, that is to say at least 1 mol of a compound with, for example, a KO group per 1 mol of aldehyde-anil. When using potassium hydroxide, the 4-fold to 8-fold quantity is preferably used.

The reaction according to the invention can generally be carried out to temperatures in the range of between about 10° and 150° C. If alcoholates are used as the potassium compound in the reaction, then the reaction frequently already succeeds at room temperature, in which case no external supply of heat is necessary. When using potassium hydroxide it is mostly necessary to work at a higher temperature. The reaction mixture is, for example, slowly warmed to 30°–100° C and is then kept at this temperature for some time, for example ½ to 2 hours. The final substances may be worked-up from the reaction mixture according to usual methods which are in themselves known.

A considerably number of in themselves new compounds the manufacture of which, however, was conceivable by devious routes only have become capable of manufacture in a simple manner according to the process described above. A further large number of new compounds could be manufactured for the first time according to the process of the invention.

The new and known compounds obtainable according to the present process generally fall within the formula

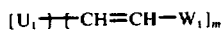 (29)

wherein in this formula $U_1$ represents an aromatic carbocyclic ring system containing 6-membered rings, which consists either (a) of a benzene ring or (b) of a condensed benzene ring system containing linearly or angularly annellated benzene rings, or (c) of several benzene rings or condensed benzene ring systems bonded to one another by C—C single bonds, or (d) represents an arrangement of several benzene rings or condensed benzene ring systems which contains at least one linkage by an unsaturated carbon atom chain having 2 or 4 carbon atoms which permits a continuous conjugation from ring to ring, whilst $W_1$ represents an aromatic carbocyclic or heterocyclic ring system containing 5 to 6 ring members which may contain still further condensed-on aromatic or hydroaromatic ring systems of carbocyclic or heterocyclic nature and which may contain aromatic or cycloaliphatic substituents of carbocyclic or heterocyclic nature as well as araliphatic and aliphatic substituents with the exception of methyl groups which in the presence of alkali metal ions are capable of carbanion formation, and $m$ represents an integer of from 1 to 4.

The index number $m$ here denotes, in the preceding formula as well as corresponding formulae, that the residue —CH=CH—$W_1$ may be present once to four times, preferably once to twice, at different points of the ring system determined by the position of the particular methyl groups of the corresponding starting substance. Both the ring system $U_1$ and also $W_1$ are at the same time in conjugation with one another, the conjugation being brought about by the ethylene bridge of the formula.

In a corresponding sense, as explained above under the definition of substitution possibilities — the rule for the possibilities of substitution in the residue $U_1$ [in formula (29) and corresponding subsequent formulae] is that all rings which are not directly bonded to a residue —CH=CH—$W_1$ may carry substituents of the 1st. order as well as carboxylic acid or carboxylic acid amide groups, whilst those benzene rings which are directly bonded to a —CH=CH—$W_1$ grouping should be free of substituents of the 2nd. order and of such substituents of the 1st. order as contain atoms which are replaceable by alkali metal, especially hydrogen atoms. In this context it must be made clear that this definition of substituents naturally relates to the structure of the immediate process products, whilst of course a subsequent introduction also of other substituents is possible by reactions which are in themselves known.

The new and known compounds accessible in accordance with the present process and of predominant interest can be circumscribed by the formula

$$[U_1 + CH=CH - W_2]_p \qquad (30)$$

wherein, in this formula, $U_1$ represents an aromatic ring system containing carbocyclic 6-membered rings which either consists (a) of a benzene ring, or (b) of a condensed benzene ring system containing linearly or angularly annellated benzene rings, or (c) of several benzene rings or condensed benzene ring systems bonded to one another by C—C single bonds, or (d) represents an arrangement of several benzene rings or condensed benzene ring systems which contains at least one linkage by an unsaturated carbon atom chain having 2 or 4 carbon atoms, which permits a continuous conjugation from ring to ring, whilst $W_2$ denotes a phenyl, diphenylyl-4, α-naphthyl, β-naphthyl, pyridyl-3, thienyl-2 or furyl-2 residue which may further contain alkoxy groups, halogen atoms, alkyl groups containing more than 1 carbon atom, dialkylamino groups and methylenedioxy groups, and wherein $p$ denotes an integer from 1 to 3.

A type of important compounds within the framework of the above formulae corresponds to the formula

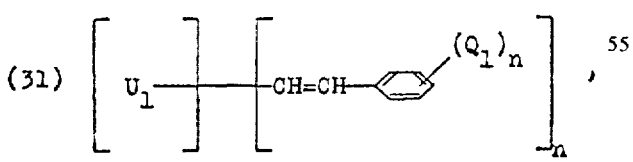

(31)

(wherein a series of members of this group has also already been manufactured in a different manner), wherein, in this formula, $U_1$ represents an aromatic ring system containing carbocyclic 6-membered rings, which either consists (a) of a benzene ring, or (b) of a condensed benzene ring system containing linearly or angularly annellated benzene rings, or (c) of several benzene rings or condensed benzene ring systems bonded to one another by C—C single bonds, or (d) represents an arrangement of several benzene rings or condensed benzene ring systems which contains at least one linkage by an unsaturated carbon atom chain with 2 or 4 carbon atoms which permits a continuous conjugation from ring to ring, whilst $Q_1$ represents a hydrogen atom, an alkoxy group, a halogen atom, an alkyl group containing more than 1 carbon atom, a dialkylamino group or a methylenedioxy group, and $n$ represents the numbers 1 or 2.

An important group of new aromatic compounds which has become accessible through the process according to the invention corresponds to the general formula

$$[U_2 + CH=CH - W_3] \qquad (32)$$

wherein, in this formula, the symbol $U_2$ represents a residue according to the partial formulae (32a) 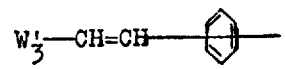

(32b) 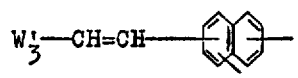

(32c) 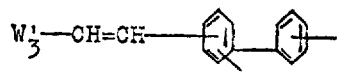

wherein the free valencies indicate at which position of $U_2$ the residue —CH=CH—$W_3$ may be located and wherein $W_3$ and $W'_3$ denote a phenyl, diphenylyl-4, α-naphthyl, β-naphthyl, Pyridyl-3, thienyl-2 or furyl-2 residue which may in each case further contain alkoxy groups, halogen atoms, alkyl groups containing more than 1 carbon atom, dialkylamino groups and methylenedioxy groups, with $W_3$ however being different from $W'_3$.

Compounds which correspond to this type may thus for example be represented by the following formulae:

(33) 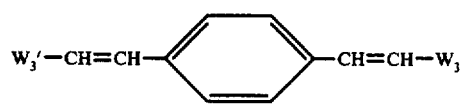

(34) 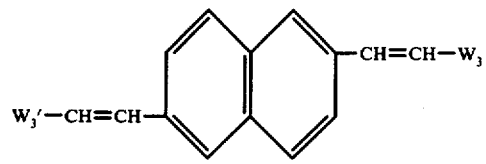

(35) 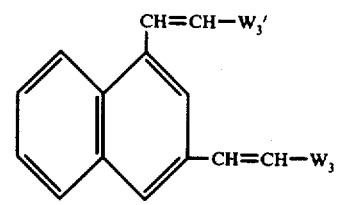

(36) 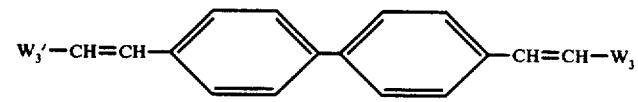

(37) 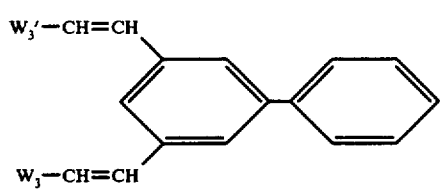

Within the framework of the definition of $W_3$ and $W'_3$, those compounds are again of predominant practical interest in which $W_3$ or $W'_3$ has the significance of a phenyl, α-naphthyl, or β-naphthyl or thienyl-3 residue and this residue may contain 1 to 2 substituents $Q_2$ having the significance of an alkoxy group containing 1 to 12 carbon atoms, an alkyl group containing 2 to 18 carbon atoms, a chlorine atom, an alkylamino group containing 2 to 18 carbon atoms or a methylenedioxy group.

In accordance with the starting substances used, important groups of the final substances obtainable according to the present process may be sub-divided as follows:

a. New compounds of formula

(38) 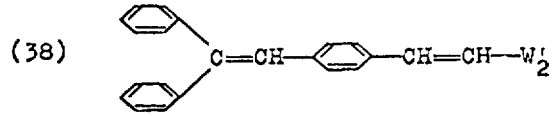

wherein $W'_2$ denotes phenyl, diphenylyl-4, naphthyl or a phenyl group which is substituted by 1 to 3 alkoxy groups having 1 to 4 carbon atoms.

b. New compounds of formula

(39) 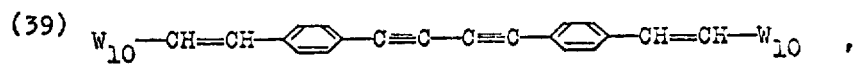

wherein $W_{10}$ denotes phenyl, diphenylyl-4, naphthyl or a phenyl residue containing 1 to 3 alkoxy groups.

c. New compounds of formula

(40) 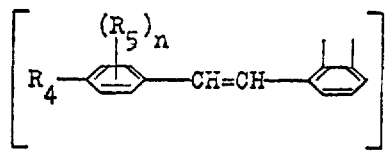

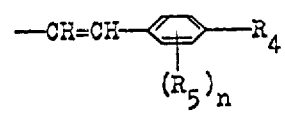

wherein $R_4$ denotes a phenyl group or an alkoxy group having 1 to 4 carbon atoms, $R_5$ denotes hydrogen or an alkoxy group having 1 to 4 carbon atoms, and n represents the numbers 1 or 2, and wherein the residue shown outside the bracket is in the ortho-position or meta-position of the phenyl residue with free valencies inside the bracket.

d. New compounds of formula

(41) 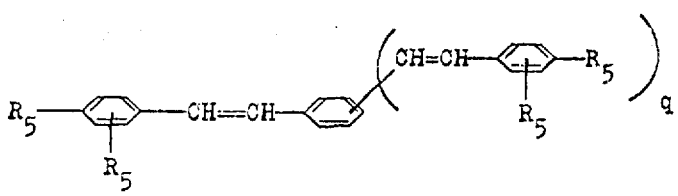

wherein R₅ denotes hydrogen or an alkoxy group having 1 to 4 carbon atoms and $q$ represents the numbers 2 or 3.

e. New and known substances of formula

(42) 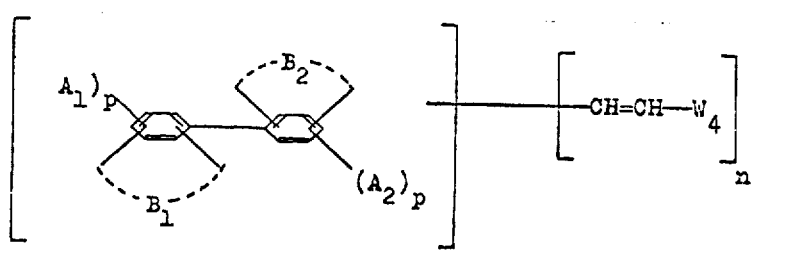

wherein the symbols $A_1$ and $A_2$ denote a hydrogen atom, or a phenyl or diphenylyl-4 residue, the symbols $B_1$ and $B_2$ are intended to represent that each of the two phenyl groups of the diphenyl skeleton may contain further linearly or angularly annellated benzene rings, p represents an integer from 1 to 3 and $W_4$ denotes an α-naphthyl, β-naphthyl, phenyl, diphenylyl-4, pyridyl-3, thienyl-2 or furyl-2 residue, with the residue $W_4$ containing 1 to 2 substituents $Q_1$ having the significance of a hydrogen atom, an alkoxy group, a halogen atom, an alkyl group containing more than 1 carbon atom, a dialkylamino group or a methylenedioxy group, and $n$ denotes an integer from 1 to 2, and wherein the free positions of the diphenyl nucleus may be occupied by substituents of the 1st. order which are free of atoms which are replaceable by alkali metal.

f. New compounds of formula

(43) $Z_1$—⟨⟩—⟨⟩—CH=CH—$W_7$ wherein $Z_1$ represents hydrogen or phenyl, and $W_7$ represents a β-naphthyl, (methylenedioxy-3,4)-phenyl or a phenyl residue

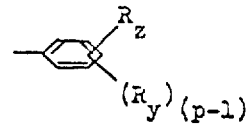

wherein $R_z$ denotes an alkyl group containing 2 to 4 carbon atoms, an alkoxy group containing 1 to 4 carbon atoms or a phenoxy group, $R_y$ represents an alkoxy group containing 1 to 4 carbon atoms, p denotes the numbers 1 to 3.

g. New and known substances of formula

(44) 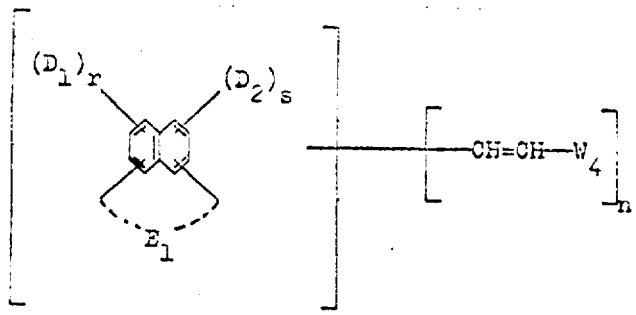

wherein the symbols $D_1$ and $D_2$ represent a hydrogen atom or a phenyl or diphenylyl-4 residue, and the symbol $E_1$ denotes that at each of the rings of the naphthyl nucleus there may be further condensed-on linearly or angularly annellated benzene rings which may in turn carry phenyl or diphenylyl-4 residues, $r$ and $s$ represent the numbers 1 to 4 to the extent that positions are still available, $W_4$ denotes an α-naphthyl, β-naphthyl, phenyl, diphenylyl-4, pyridyl-3, thienyl-2 or furyl-2 residue with the residue $W_4$ containing 1 to 2 substituents $Q_1$ having the significance of a hydrogen atom, an alkoxy group, a halogen atom, an alkyl group containing more than 1 carbon atom, a dialkylamino group or a methylenedioxy group, $n$ denotes an integer from 1 to 2 and wherein the free positions of the naphthalene nucleus may be occupied by substituents of the 1st. order which are free of atoms which are replaceable by alkali metal.

h. New compounds of formula

(45) 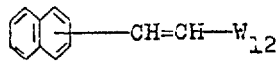

wherein $W_{12}$ denotes diphenylyl-4, pyrenyl-1, (4-phenoxy)phenyl or a phenyl residue containing 1 to 3 alkoxy groups with 1 to 4 carbon atoms.

i. New and known substances of formula

(46) 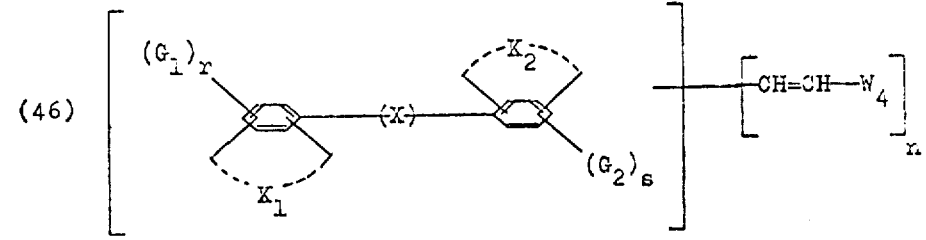

wherein, in this formula X denotes a bridge member of the series —CH=CH—, —CH=CH—CH=CH—, —C≡C—, the symbols $G_1$ and $G_2$ represent hydrogen atoms or phenyl groups, $r$ and $s$ each represents an integer from 1 to 3 and the symbols $K_1$ and $K_2$ are intended to represent that each of the two phenyl groups of the formula can contain further linearly or angularly annellated benzene rings, $W_4$ denotes an α-naphthyl, β-naphthyl, phenyl, diphenylyl-4, pyridyl-3, thienyl-2 or furyl-2 residue with the residue $W_4$ containing 1 to 2 substituents $Q_1$ having the significance of a hydrogen atom, an alkoxy group, a halogen atom, an alkyl group containing more than 1 carbon atom, a dialkylamino group or a methylenedioxy group, and $n$ denotes an integer from 1 to 2, and wherein the free positions of the phenyl nucleus may be occupied by substituents of the 1st. order which are free of atoms which are replaceable by alkali metal.

k. New compounds of formula

(47) 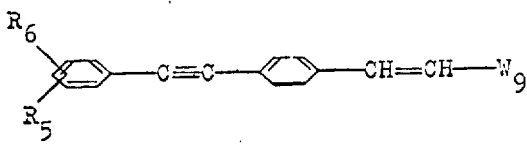

wherein $W_9$ represents an α-naphthyl, β-naphthyl, diphenyl-4, thienyl-2, pyridyl-3, (methylenedioxy-3,4)-phenyl or a phenyl residue

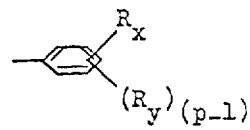

wherein $R_x$ denotes halogen, an alkyl group containing 2 to 4 carbon atoms, a phenoxy group or an alkoxy group containing 1 to 4 carbon atoms, $R_y$ represents an alkoxy group containing 1 to 4 carbon atoms and $p$ represents the numbers 1 to 3, $R_6$ denotes hydrogen, an alkoxy group having 1 to 4 carbon atoms or a phenyl group, and $R_5$ represents hydrogen or an alkoxy group having 1 to 4 carbon atoms.

l. New compounds of formula

(48) 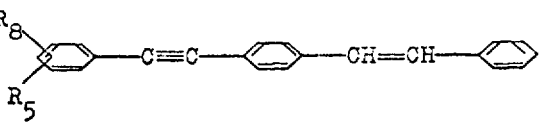

wherein $R_5$ denotes hydrogen or an alkoxy group having 1 to 4 carbon atoms and $R_8$ denotes phenyl or an alkoxy group having 1 to 4 carbon atoms.

m. New compounds of formula (49)

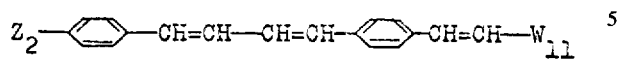

wherein $Z_2$ denotes hydrogen or a residue $W_{11}$—CH=CH—, and $W_{11}$ represents α-naphthyl, β-naphthyl, diphenylyl-4 or a phenyl group of formula

wherein $R_v$ denotes halogen, an alkyl group having 2 to 4 carbon atoms or an alkoxy group having 1 to 4 carbon atoms.

n. New compounds, according to claim 32, of formula (50)

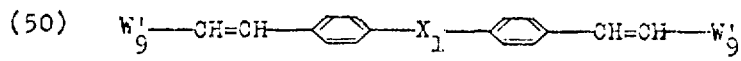

wherein $X_1$ denotes a linkage member —CH=CH— or —C≡C— and $W'_9$ represents α-naphthyl, β-naphthyl, diphenylyl-4, thienyl-2, (methylenedioxy-3,4)-phenyl or a phenyl residue

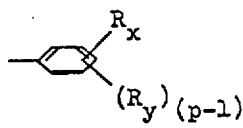

wherein $R_x$ denotes halogen, an alkyl group containing 2 to 4 carbon atoms, a phenoxy group or an alkoxy group containing 1 to 4 carbon atoms, $R_y$ represents an alkoxy group containing 1 to 4 carbon atoms and p represents the numbers 1 to 3.

o. New and known substances of formula (51)

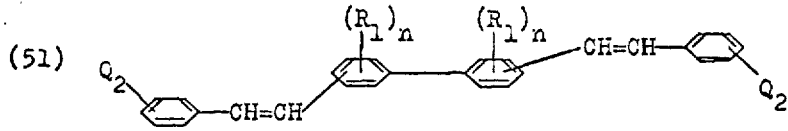

wherein the styryl residues of this formula are preferably located in the 4,4'-position of the diphenyl nucleus, $Q_2$ represents a hydrogen atom, an alkyl group containing 2 to 18 carbon atoms, an alkoxy group containing 1 to 12 carbon atoms, a chlorine atom or a methylenedioxy group, $R_1$ represents hydrogen or other substituents of the 1st. order which are free of atoms which are replaceable by alkali metal and n denotes an integer from 1 to 2.

p. New compounds of formula (52)

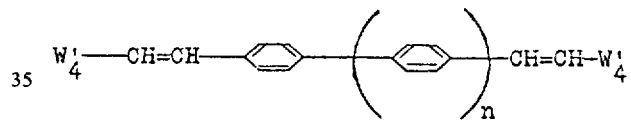

wherein $W'_4$ represents an α-naphthyl, β-naphthyl, diphenylyl-4, (methylenedioxy-3,4)-phenyl or a phenyl residue

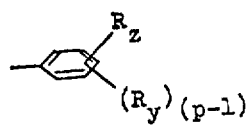

wherein $R_z$ denotes an alkyl group containing 2 to 4 carbon atoms, an alkoxy group containing 1 to 4 carbon atoms or a phenoxy group, $R_y$ represents an alkoxy group containing 1 to 4 carbon atoms, and p denotes the numbers 1 to 3 and n represents the numbers 1 or 2.

q. New compounds of formula

(53) 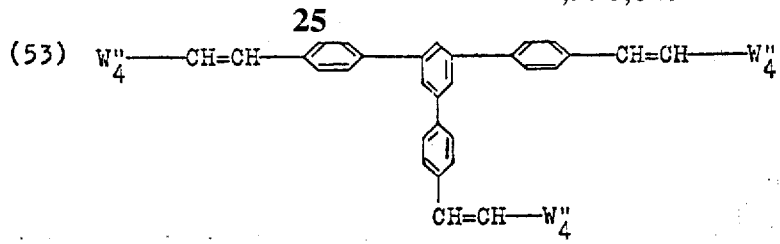

wherein W'''₄ represents phenyl, α-naphthyl, β-naphthyl, diphenylyl-4 or a phenyl group which may contain 1 to 3 alkoxy groups having 1 to 4 carbon atoms.

r. New and known substances of formula

(54) 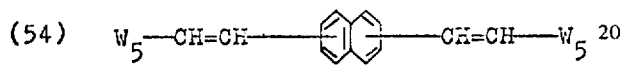

wherein the residues —CH=CH—W₅ are preferably located in the 2,6-positions and W₅ denotes a phenyl, α-naphthyl, β-naphthyl or thienyl-2 residue which may contain still further substitutents, preferably 1 to 2 in number, of the group of halogen, alkyl, alkoxy and alkylamino having in each case up to 18 carbon atoms, a phenyl residue which is optionally substituted by the substitutents listed above, or a condensed-on hydroaromatic carbocyclic 6-membered ring or methylenedioxy ring.

s. New compounds of formula

(55) 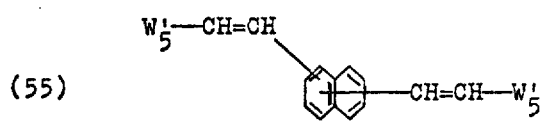

wherein the residues W'₅ occupy the positions 2:3, 1:3, 1:4, 1:5, 1:6 or 1:7 and W'₅ represents an α-naphthyl, β-naphthyl, diphenylyl-4, thienyl-2 or a phenyl residue

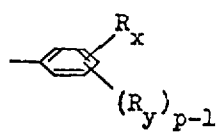

wherein $R_x$ denotes halogen, an alkyl group containing 2 to 4 carbon atoms, a phenoxy group or an alkoxy group containing 1 to 4 carbon atoms, $R_y$ represents an alkoxy group containing 1 to 4 carbon atoms, $p$ represents the numbers 1 to 3.

t. New compounds of formula

(56) 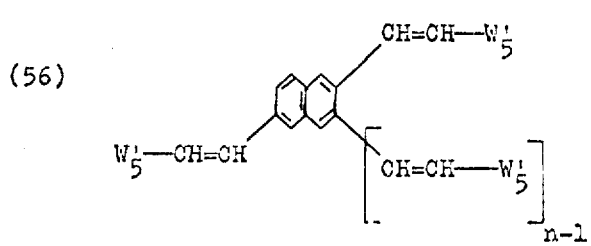

wherein W'₅ represents diphenylyl-4, α-naphthyl, β-naphthyl, thienyl-2 or a phenyl residue wherein $R_z$ denotes an alkyl group containing 2 to 4 carbon atoms, an alkoxy group containing 1 to 4 carbon atoms or a phenoxy group, $R_y$ represents an alkoxy group containing 1 to 4 carbon atoms, $p$ denotes the numbers 1 to 3 and n represents the numbers 1 or 2.

u. New and known substances of formula

(57) 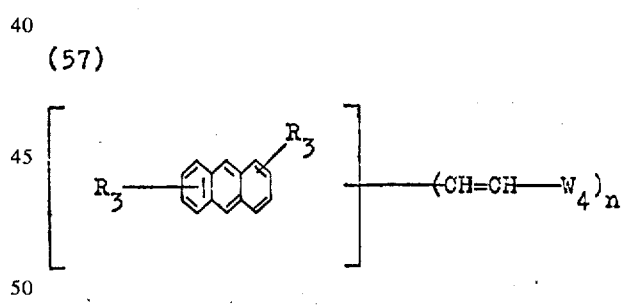

wherein W₄ denotes an α-naphthyl or β-naphthyl, phenyl, diphenylyl-4, pyridyl-3, thienyl-2 or furyl-2 residue with the residue W₄ containing 1 to 2 substitutents Q₁ having the significance of a hydrogen atom, an alkoxy group, a halogen atom, an alkyl group containing more than 1 carbon atom, a dialkylamino group or a methylenedioxy group, and n denotes an integer from 1 to 2, and R₃ represents halogen or phenyl.

v. New compounds of formula

(58) 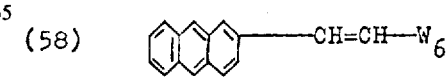

wherein $W_6$ represents phenyl, α-naphthyl, β-naphthyl, diphenylyl-4, thienyl-2, pyridyl-3, (methylenedioxy-3,4)phenyl or a phenyl residue

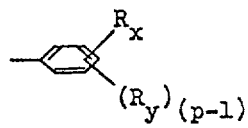

wherein $R_x$ denotes halogen, an alkyl group containing 2 to 4 carbon atoms, a phenoxy group or an alkoxy group containing 1 to 4 carbon atoms, $R_y$ represents an alkoxy group containing 1 to 4 carbon atoms and $p$ represents the numbers 1 to 3.

w. New compounds of formula (59)

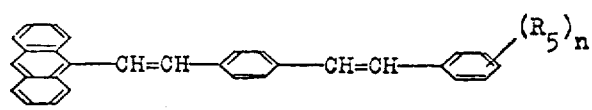

wherein $R_5$ represents hydrogen or an alkoxy group containing 1 to 4 carbon atoms and $n$ denotes the numbers 1 or 2.

x. New and known substances of formula (60)

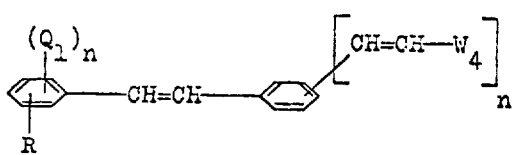

wherein $Q_1$ denotes a hydrogen atom, an alkoxy group, a halogen atom, an alkyl group containing more than 1 carbon atom, a dialkylamino group or a methylenedioxy group, $n$ denotes an integer of from 1 to 2, and $W_4$ denotes an α-naphthyl, β-naphthyl phenyl, diphenylyl-4, pyridyl-3, thienyl-2 or furyl-2 residue, with the residue $W_4$ containing 1 to 2 substituents $Q_1$ having the significance of a hydrogen atom, an alkoxy group, a halogen atom an alkyl group containing more than 1 carbon atom, a dialkylamino group or a methylenedioxy group and n denoting an integer from 1 to 2, $R_2$ represents hydrogen and the residue —CH=CH—$W_4$ is preferably located in the p-position to the stilbene double bond.

y. New aromatic compounds of general formula (61)

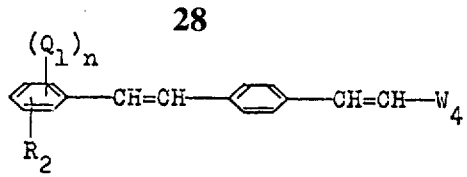

wherein $Q_1$ denotes a hydrogen atom, an alkoxy group, a halogen atom, an alkyl group containing more than 1 carbon atom. a dialkylamino group or a methylenedioxy group, n denotes an integer from 1 to 2, $R_2$ denotes hydrogen, $W_4$ denotes an α-naphthyl, β-naphthyl, diphenylyl-4, pyridyl-3, thienyl-2 or furyl-2 residue with the residue $W_4$ containing 1 or 2 substituents $Q_1$ having the significance of a hydrogen atom, an alkoxy group or a halogen atom, an alkyl group containing more than 1 carbon atom, a dialkylamino group or a methylenedioxy group, and n denotes an integer from 1 to 2, with the residue

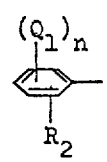

according to the above formula being different from $W_4$.

$z_1$. New compounds of formula (62)

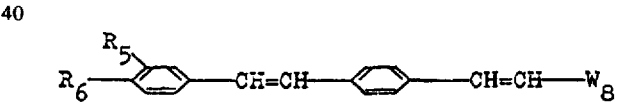

wherein $W_8$ represents α-naphthyl, β-naphthyl, thienyl-2, pyridyl-3, (methylenedioxy-3,4)-phenyl or a phenyl residue

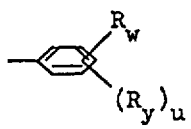

wherein $R_w$ denotes halogen, an alkyl group containing 2 to 4 carbon atoms or a phenoxy group, $R_y$ represents an alkoxy group containing 1 to 4 carbon atoms and $u$ represents the numbers 0, 2 to 3, $R_5$ represents hydrogen or an alkoxy group having 1 to 4 carbon atoms and $R_6$ represents hydrogen, an alkoxy group having 1 to 4 carbon atoms or a phenyl group.

$z_2$. New compounds of formula (63)

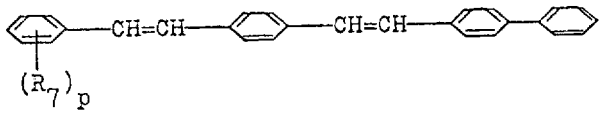

wherein $R_7$ represents an alkoxy group having 1 to 4 carbon atoms and $p$ represents the numbers 1, 2 or 3.

As regards the possibilities of substitution in these abovementioned substances, the rules are completely analogous to what has been explained in more detail in describing the starting substances. From the specific point of view of usability as optical brightening agents, substitution by non-chromophoric substituents is of especial importance.

Amongst the large number of possible non-chromophoric substituents in the abovementioned formulae, there may for example be mentioned, as being for practical purposes of predominant interest, halogen, alkyl groups, alkoxy groups, cycloalkyl groups, aralkyl groups, phenyl groups, hydroxyl groups, amino groups, carboxyl groups as well as their substitutive and functional derivatives. Herein it goes without saying that such non-chromophoric substituents as do not meet the requirements according to the general substituent definition, whilst having to be excluded in the starting substances, can on the other hand be undoubtedly present in the reaction end products, by being subsequently introduced according to methods which are in themselves known. Amongst substitutive or functional derivatives of such non-chromophoric groups as are indicated above, there may be quoted as examples: halogenalky, hydroxyalkyl, cyanalkyl, carboxyalkyl and phenylalkyl groups; carboxylic acid esters, amides, halides, nitriles and hydrazides; alkoxy, aralkoxy, phenoxy or hydroxyalkoxy groups; alkylated, arylated or acylated amino groups, amino groups substituted by 1,3,5-triazinyl residues, and the like.

The compounds which can be manufactured according to the new process may serve as intermediates for syntheses of the most diverse nature, for example for the manufacture of dyestuffs and pharmaceuticals. These compounds may also be modified by the introduction of further substituents according to methods which are in themselves known, for example the introducton of chloromethyl groups, oxidation of methyl groups, halogenation and the like.

A large number of compounds which fall under formulae (29) to (63) may — to the extent that they show a blue to violet fluorescence — be used as optical brighteners. Such a fluorescence which can be utilised for purposes of optical brightening is generally present if emission maxima lie within the range of about 410 to 450 m$\mu$. Amongst the new compounds obtainable according to this process, those compounds should especially be highlighted as optical brighteners which correspond to formulae (43), (47), (48), (50), (56), (58), (61), (62) or (63). In addition, the general formulae further comprise a large number of optically brightening compounds which are currently of lesser practical importance, for example compounds of formulae (275), (276) or (282).

The types of compounds which have been highlighted above as regards their brightener action possess a more or less pronounced fluorescence in the dissolved or finely divided state. They are suitable for the optical brightening of the most diverse organic materials of natural or synthetic origin, or of materials containing such organic substances for which an optical brightening is to be considered. The following groups of organic materials may for example be mentioned as such materials, without the list which follows being intended to express any restriction thereof:

I. Synthetic organic high molecular materials such as

A. Polymerisation products based on organic compounds containing at least one polymerisable carbon-carbon double bond (homopolymers or copolymers as well as their post-treatment products such as crosslinking products, grafting products or degradation products, polymer dilutions and the like), for which the following may be mentioned by way of example: polymers based on $\alpha,\beta$-unsaturated carboxylic acids (for example acrylic compounds), on olefine hydrocarbons, on vinyl and vinylidene compounds, on halogenated hydrocarbons, on unsaturated aldehydes and ketones, allyl compounds and the like; furthermore, polymerisation products such as are obtainable by ring opening (for example polyamides of the polycaprolactam type), and furthermore formaldehyde polymers, or polymers which are obtainable both by polyaddition and also polycondensation, such as polythioethers, polyacetals and thioplastics.

B. Polycondensation products or pre-condensates based on bifunctional or polyfunctional compounds having groups capable of condensation, their homocondensation or co-condensation products, as well as products of post-treatment (for example polyesters, saturated and unsaturated, unbranched as well as branched), polyamides, maleate resins, their pre-condensates and products of analogous structure, polycarbonates, silicone resins and others;

C. polyaddition products such as polyurethanes (crosslinked and un-crosslinked), and epoxide resins.

II. Semi-synthetic organic materials such as for example cellulose esters, nitrocellulose, cellulose ethers, regenerated cellulose or their post-treatment products, and casein plastics.

III. Natural organic materials of animal or vegetable origin, for example based on cellulose or proteins such as wool, cotton, silk, leather, finely divided wood compositions, natural resins, and furthermore rubber, guttapercha, balata as well as their post-treatment products and modification products.

The possible organic materials may be present in the most diverse processing states (raw materials, semi-finished goods or finished goods) and states of aggregation. They may, on the one hand, be present in the form of the most diverse shaped structures, for example as sheets, profiles, injection mouldings, chips, granules or foams; films, foils, lacquers, bands, coverings, impregnations and coatings or filaments, fibres, flocks, bristles and wires. The materials mentioned may on the other hand also be present in unshaped states in the most diverse homogeneous and inhomogeneous forms of division and states of aggregation, for example as powders, solutions, emulsions, dispersions, sols, gels, putties, pastes, waxes, adhesives and trowelling compositions and the like.

Fibre materials may for example be present as endless filaments, staple fibres, flocks, hanks, yarns, threads, fibre fleeces, felts, waddings, flocked structures, textile woven fabrics or laminates, knitted fabrics as well as paper, cardboards or paper compositions and the like.

For use as brighteners, these compounds may be added to the materials mentioned before or during shaping. Thus they may for example, when manufacturing films or other shaped articles, be added to the moulding composition or dissolved, dispersed or otherwise finely divided in the spinning composition before spinning. The optical brighteners may also be added to the starting substances, reactions mixtures or intermediates for the manufacture of fully synthetic or semi-synthetic organic materials, that is to say also before or during the chemical reaction, for example in the case of a polycondensation, a polymerisation or a polyaddition.

The new optical brighteners may of course also be employed in all cases where organic materials of the nature indicated above are combined with inorganic materials in any form. They are distinguished by a particularly good heat stability, fastness to light and migration resistance.

The amount of the new optical brighteners to be used, relative to the material to be optically brightened, may vary within wide limits. A distinct and durable effect can already be achieved with very small quantities, in certain cases for example quantities of 0.001% by weight. It is however also possible to employ quantities of up to 0.5 % by weight and above. For most practical purposes, amounts of between 0.01 and 0.2 % by weight are preferably of interest.

The compounds serving as brighteners may for example also be employed as follows: (a) mixed with dyestuffs or pigments or as an additive to dye baths, and printings, etching or reserve pastes. Furthermore also for the post-treatment of dyeings, prints or discharge prints, (b) mixed with so-called "carriers", anti-oxidants, light protection agents, heat stabilisers, chemical bleaching agents, or as an additive to bleaching baths, (c) mixed with crosslinking agents, finishing agents such as starch or synthetically acessible finishes, (d) in combination with detergents, wherein the detergents and brighteners may be separately added to the wash baths to be used, or wherein advantageously detergents are used which contain the admixed brightener, (e) in combination with polymeric carriers (polymerisation, polycondensation or polyaddition products) in which the brighteners are introduced in a dissolved or dispersed form, optionally along with other substances, (f) as additives to the most diverse industrial products in order to make these more marketable or to avoid disadvantages in usability, for example as an additive to glues, adhesives, paints and the like, and (g) in combination with optical brighteners of other constitutions.

The compounds which have been highlighted as optical brighteners can also be used as scintillators, for various purposes of a photographic nature such as for electrophotographic reproduction or for super-sensitisation. Above all the compounds which absorb in the short-wave range are suitable as scintillators, ultra-violet absorbers or for electrophotographic purposes. On the other hand the compounds which absorb in the long-wave range represent good fluorescence dyestuffs.

For example, the compounds according to the general formulae (102), (107), (119), (158), (282) or (360) may be used as scintillators whilst for example the compounds according to general formulae (202), (203), (246), (252), (271), (275) or (276) represent good fluorescence dyestuffs.

As examples of compounds which may serve as ultra-violet absorbers, those of general formulae (207) and (208) may be mentioned.

In the tables which follow below, the columns denote:
COLUMN I = Formula number
COLUMN II = Structural elements
COLUMN III = Melting points (uncorrected) in °C.

EXAMPLE 1

2.65 g of o-xylene, 10.56 g of 4'-methoxy-benzalaniline and 11.2 g of potassium tertiary-butylate are stirred in 200 ml of anhydrous dimethylformamide with exclusion of air, whereupon a brown colouration is produced. The temperature is brought to 90° C over the course of 30 minutes and the mixture is stirred for 1 hour at 90° to 95° C and thereafter cooled to room temperature. 150 ml of water and 150 ml of 10% strength aqueous hydrochloric acid are now successively added dropwise. The precipitated reaction product is filtered, washed with a large amount of water and thereafter with 200 ml of methanol and dried: 4.1g (48 % of theory) of 1,2-di-(4'-methoxy-styryl)-benzene of formula

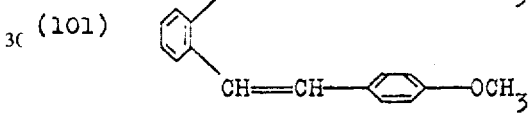

(101)

in the form of a light beige powder, melting point 122° to 123° C. Three recrystallisations from dioxane-ethanol-water (active charcoal) yields 3.0 g (35.1 % of theory) of colourless felted small needles of melting point 124.5° to 125° C. Analysis: $C_{24}H_{22}O_2$. Calculated: C 84.17, H 6.47, N 9.35; found: C 84.00, H 6.43, N 9.32.

The 1,2-distyryl-benzene derivatives of formula

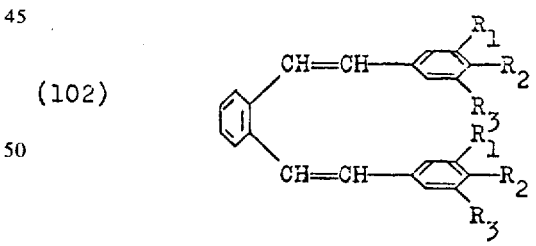

(102)

listed in the Table which follows can be manufactured in a similar manner from o-xylene:

| I | II | | | III |
| --- | --- | --- | --- | --- |
| | $R_1$ | $R_2$ | $R_3$ | |
| 103 | H | H | H | 118 – 118.5 |
| 104 | H | ⌬ | | H | 204 – 206 |
| 105 | —OCH₃ | —OCH₃ | H | 174 – 174.5 |
| 106 | —OCH₃ | —OCH₃ | —OCH₃ | 160 – 160.5 |

The 1,3-distyryl-benzene derivatives of formula (107) 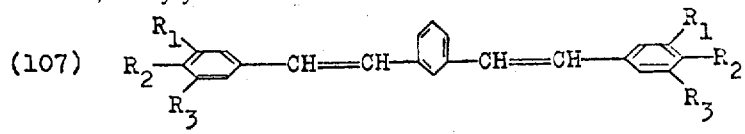

(115) 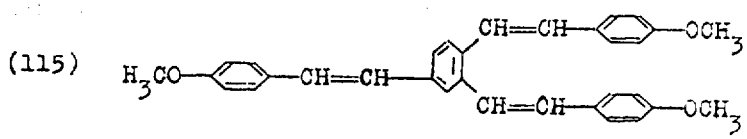

listed in the Table which follows can be manufactured in a similar manner from m-xylene:

| I | II R$_1$ | R$_2$ | R$_3$ | III |
|---|---|---|---|---|
| 108 | H | —OCH$_3$ | H | 224 – 224.5 |
| 109 | —OCH$_3$ | —OCH$_3$ | H | 178.5 – 179 |
| 110 | —OCH$_3$ | —OCH$_3$ | —OCH$_3$ | 136.5 – 137 |

The 1,4-distyryl-benzene derivatives of formula (111) 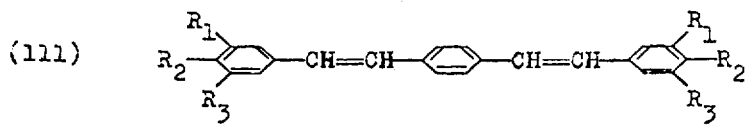

listed in the Table which follows can be manufactured in a similar manner from p-xylene:

| I | II R$_1$ | R$_2$ | R$_3$ | III |
|---|---|---|---|---|
| 112 | H | —OCH$_3$ | H | 308 – 309 |
| 113 | —OCH$_3$ | —OCH$_3$ | H | 266 – 267 |
| 114 | —OCH$_3$ | —OCH$_3$ | —OCH$_3$ | 203 – 204 |

EXAMPLE 2

2.0 g of 1,3,4-trimethylbenzene, 15.8 g of 4′-methoxybenzalaniline and 11.2 g of potassium tertiary-butylate are reacted in 150 ml of anhydrous dimethylformamide in accordance with the data of example 1: 2.95 g (37.4 % of theory) of 1,3,4-tri-(4′-methoxy-styryl)-benzene of formula in the form of a light yellow powder, melting point 165° to 167° C. Two recrystallisations from isopropanol (active charcoal) yield 2.0 g (25.3 % of theory) of light greenish-tinged yellow, felted small needles of melting point 173° to 173.5° C.

Analysis: C$_{33}$H$_{30}$O$_3$. Calculated: C 83.51, H 6.37, O 10.11; found: C 83.52, H 6.10, O 10.29.

The 1,3,4-tristyryl-benzene derivatives of formula (116) 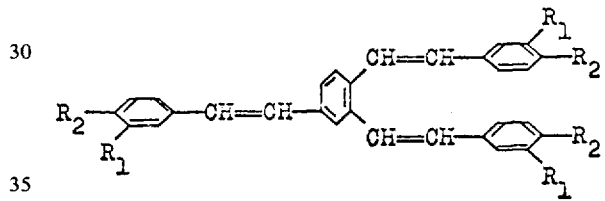

listed in the Table which follows can be manufactured in a similar manner from 1,3,4-trimethylbenzene:

| I | II R$_1$ | R$_2$ | III |
|---|---|---|---|
| 117 | H | H | 187 – 187.5 |
| 118 | —OCH$_3$ | —OCH$_3$ | 196 – 196.5 |

The 1,3,5-tristyryl-benzene derivatives of formula (119) 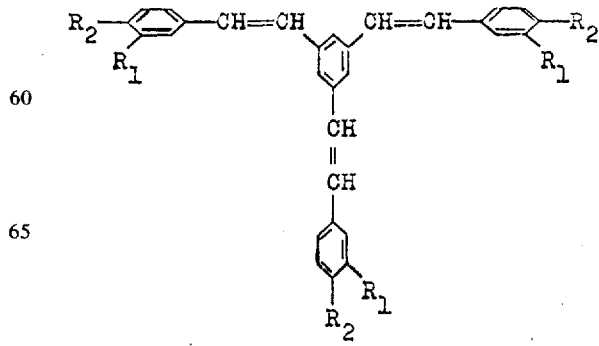

listed in the Table which follows can be manufactured in a similar manner from 1,3,5-trimethylbenzene

| I | II R$_1$ | II R$_2$ | III |
|---|---|---|---|
| 120 | H | H | 203 – 203.5 |
| 121 | H | —OCH$_3$ | 161 – 161.5 |
| 122 | —OCH$_3$ | —OCH$_3$ | 148 – 148.5 |

The 1,2,3,4-tetra-(4'-methoxy-styryl)-benzene of formula (123)

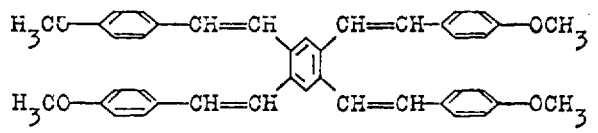

can be manufactured in a similar manner from 1,2,3,4-tetramethylbenzene and 4'-methoxy-benzalaniline: light greenish-tinged yellow fine felted small needles from xylene; melting point 238° to 239° C. Analysis: C$_{42}$H$_{38}$O$_4$. Calculated: C 83.14, H 6.31, O 10.55; found: C 83.46, H 6.38, O 10.50.

EXAMPLE 3

1.68 g of 4-methyl-biphenyl, 1.81 g of benzalaniline and 2.24 g of potassium tertiary-butylate are stirred in 80 ml of anhydrous dimethylformamide with exclusion of air, whereupon a reddish-brown clear solution is produced. The temperature is brought to 90° C over the course of 30 minutes and the mixture is stirred for 1 hour at 90° to 95° C and thereafter cooled to room temperature. 70 ml of water and 60 ml of 10% strength aqueous hydrochloric acid are now successively added dropwise. The precipitated reaction product is filtered off, washed with a large amount of water and thereafter with 80 ml of methanol and dried: 2.1 g (82.0 % of theory) of 4-styryl-biphenyl of formula (124) 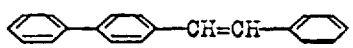

in the form of a light beige powder, melting point 221.5° to 222° C. Two recrystallisations from dioxane-ethanol (active charcoal) yield 1.7 g (66.4 % of theory) of colourless glistening platelets and small needles of melting point 222.5° to 223° C.

Analysis: C$_{20}$H$_{16}$. Calculated C 93.71, H 6.29; found: C 93.94, H 6.37.

The 4-styryl-biphenyl derivatives of formula (125) 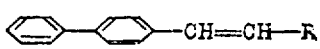

listed in the Table which follows can be manufactured in a similar manner:

| I | II R | III |
|---|---|---|
| 126 | ⌬—OCH$_3$ | 237 – 238 |
| 127 | ⌬ with OCH$_3$, OCH$_3$ | 183.5 – 184 |
| 128 | ⌬ with OCH$_3$, OCH$_3$, OCH$_3$ | 153 – 154 |
| 129 | ⌬—O—⌬ | 213 – 214 |
| 130 | ⌬—⌬ | 307 – 308 |
| 131 | ⌬ with O—CH$_2$—O | 188.5 – 189 |
| 132 | ⌬—N(C$_2$H$_5$)$_2$ | 174 – 174.5 |
| 133 | naphthyl | 231 – 232 |

The 4-styryl-p-terphenyl derivatives of formula (135) 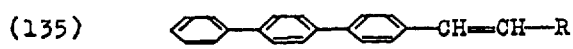

listed in the Table which follows can be manufactured in a similar manner from 4-methyl-p-terphenyl:

| I | II R | III |
|---|---|---|
| 134 | (naphthyl) | 222 – 223 |
| 136 | (phenyl) | 315 – 316 |
| 137 | (—C₆H₄—OCH₃) | 327 – 328 |
| 138 | (biphenyl) | 367 – 368 |
| 139 | (methylenedioxyphenyl) | 278 – 279 |
| 140 | (naphthyl) | 312 – 313 |
| 141 | (naphthyl) | 223 – 225 |

EXAMPLE 4

2.30 g of 4,4'-dimethyl-biphenyl, 8.1 g of 4'-methoxybenzalaniline and 5.6 g of potassium tertiary-butylate are reacted in 150 ml of anhydrous dimethylformamide in accordance with the data of example 3: 4.9 g (94.3 % of theory) of 4,4'-di-(4''-methoxy-styryl)-biphenyl of formula (142) 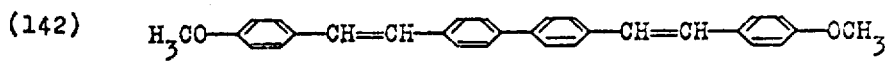

in the form of a light yellow powder, melting point 353° to 354° C. Three recrystallisations from o-dichlorobenzene (active charcoal) yield 3.1 g (59.6% of theory) of light greenish-tinged yellow fine glistening small needles of melting point 357° to 358° C.

Analysis: $C_{30}H_{26}O_2$. Calculated: $C_{86.09}$, H 6.26, O 7.65; found: C 86.09, H 6.44, O 7.74.

The 4,4'-distyryl-biphenyl derivatives of formula (143) 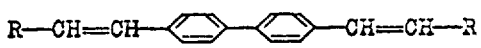

listed in the Table which follows can be manufactured in a similar manner:

| I | II R | III |
|---|---|---|
| 144 | (phenyl) | 330 – 331 |
| 145 | (—C₆H₄—CH(CH₃)₂) | 318 – 319 |

-continued

| I | II R | III |
|---|---|---|
| 146 | biphenyl | >400 |
| 147 | diphenyl ether | 346 - 347 |
| 148 | 3,4-dimethoxyphenyl | 321 - 322 |
| 149 | 3,4,5-trimethoxyphenyl | 234 - 235 |
| 150 | methylenedioxyphenyl (with OCH₃) | 319 — 320 |
| 151 | 2-naphthyl | 360 - 361 |
| 152 | 1-naphthyl | 274 - 275 |

The 4,4''-distyryl-p-terphenyl derivatives of formula (153)

R—CH=CH—⟨⟩—⟨⟩—⟨⟩—CH=CH—R listed in the Table which follows can be manufactured in a similar manner from 4,4''-dimethyl-p-terphenyl:

| I | II R | III |
|---|---|---|
| 154 | phenyl | >380 |
| 155 | 4-isopropylphenyl | >380 |
| 156 | 4-methoxyphenyl | >380 |
| 157 | 2-naphthyl | 331 - 332 |

The 1,3,5-tristilbenyl-benzene derivatives of formula (158)

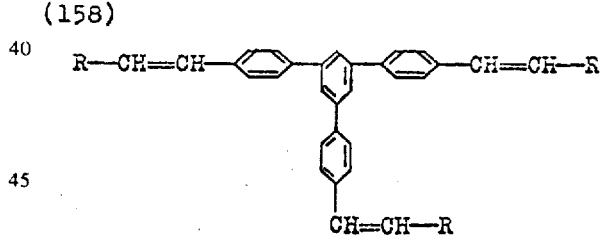

listed in the Table which follows can be manufactured in a similar manner from 1,3,5-tri-(p-tolyl)-benzene.

| I | II R | III |
|---|---|---|
| 159 | phenyl | 212 - 212.5 |
| 160 | 4-methoxyphenyl | 219 - 220 |

-continued

| I | II R | III |
|---|---|---|
| 161 | ![phenyl with two OCH₃] | 171 – 171.5 |
| 162 | ![phenyl with three OCH₃] | 167.5 – 168 |
| 163 | ![biphenyl] | 349 – 350 |
| 164 | ![naphthyl] | 269 – 270 |
| 165 | ![naphthyl] | 276 – 277 |

EXAMPLE 5

4.85 g of 4-methyl-stilbene, 4.54 g of benzalaniline and 12.5 g of potassium hydroxide powder containing about 10% of water are stirred in 150 ml of dimethylformamide with exclusion of air, whereupon a dark blue colouration is produced. The temperature is brought to 90° C over the course of 30 minutes and the mixture is stirred for a further 1 hour at 90° to 95° C, whereupon the reaction product is produced in a crystalline form. After cooling to room temperature 100 ml of water and 150 ml of 10% strength aqueous hydrochloric acid are successively added dropwise. The product is filtered off, first washed with a large amount of water and thereafter with 300 ml of methanol, and dried. 6.4 g (90.7% of theory) of 1,4-distyryl-benzene of formula (166)

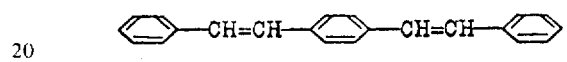

in the form of a light yellow powder, melting point 265° to 265.5° C. Three recrystallisations from xylene (active charcoal) yield 5.9 g (83.6% of theory) of pale greenish-tinged yellow felted small needles of melting point 265.5° C. Analysis: $C_{22}H_{18}$. Calculated: C 93.57, H 6.43; found: C 93.37, H 6.42.

The 1,4-distyryl-benzene derivatives of formula (167)

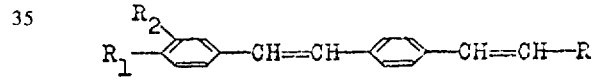

listed in the Table which follows can be manufactured in a similar manner:

| I | II R | | III |
|---|---|---|---|
| | | $R_1$ | $R_2$ |
| 168 | ![phenyl-Cl] | H | H | 277 – 278 |
| 169 | ![phenyl-CH(CH₃)₂] | H | H | 235 – 236 |
| 170 | ![phenyl-OCH₃] | H | H | 274 – 275 |

-continued

| I | II R | R₁ | R₂ | III |
|---|---|---|---|---|
| 171 | 3,4-dimethoxyphenyl | H | H | 221 – 222 |
| 172 | 2,3,4-trimethoxyphenyl | H | H | 205 – 205.5 |
| 173 | 4-phenoxyphenyl | H | H | 246 – 247 |
| 174 | 4-biphenylyl | H | H | 318 – 319 |
| 175 | 2-naphthyl | H | H | 266 – 267 |
| 176 | 1-naphthyl | H | H | 178.5 – 179 |
| 177 | 3,4-methylenedioxyphenyl (benzodioxole) | H | H | 245 – 246 |
| 178 | 2-thienyl | H | H | 258 – 259 |
| 179 | 3-pyridyl | H | H | 234 – 235 |
| 180 | phenyl | —OCH₃ | H | 274 – 275 |

| I | II R | R₁ | R₂ | III |
|---|---|---|---|---|
| 181 | 4-isopropylphenyl | —OCH₃ | H | 269 – 271 |
| 182 | 4-methoxyphenyl | —OCH₃ | H | 306 – 307 |
| 183 | 3,4-dimethoxyphenyl | —OCH₃ | H | 235 – 236 |
| 184 | 3,4,5-trimethoxyphenyl | —OCH₃ | H | 199.5 – 200 |
| 185 | 4-phenoxyphenyl | —OCH₃ | H | 272 – 273 |
| 186 | 4-biphenylyl | —OCH₃ | H | 334 – 335 |
| 187 | 2-naphthyl | —OCH₃ | H | 287 – 288 |
| 188 | 1-naphthyl | —OCH₃ | H | 197.5 – 198 |
| 189 | 3,4-methylenedioxyphenyl | —OCH₃ | H | 260 – 261 |
| 190 | 4-isopropylphenyl | —OCH₃ | —OCH₃ | 227 – 228 |

| I | II R | III R₁ | R₂ | |
|---|---|---|---|---|
| 191 | -C₆H₄-O-C₆H₅ | —OCH₃ | —OCH₃ | 219 – 220 |
| 192 | -C₆H₄-C₆H₅ | —OCH₃ | —OCH₃ | 284 – 285 |
| 193 | 2,3,4-trimethoxyphenyl | —OCH₃ | —OCH₃ | 161 – 161.5 |
| 194 | pyridyl | —OCH₃ | —OCH₃ | 190 – 190.5 |
| 195 | phenyl | phenyl | H | 317 – 318 |
| 196 | 4-isopropylphenyl | phenyl | H | 322 – 323 |
| 197 | 4-methoxyphenyl | phenyl | H | 331 – 332 |
| 198 | biphenyl | phenyl | H | 372 – 373 |
| 199 | naphthyl | phenyl | H | 320 – 321 |
| 200 | naphthyl | phenyl | H | 247 – 248 |

EXAMPLE 6

4.77 g of 4'-methyl-stilbene-4-carboxylic acid, 3.70 g of benzalaniline and 11.2 g of potassium tertiary-butylate in 150 ml of anhydrous dimethylformamide are stirred with exclusion of air, whereupon a violet colouration is produced. The temperature is raised to 60° C over the course of 30 minutes, and the mixture is stirred for 1 hour at 60° to 65° C and cooled to room temperature. 100 ml of water and 140 ml of 10 % strength aqueous hydrochloric acid are now successively added dropwise. The precipitated reaction product is filtered off, washed with a large amount of water and then with 200 ml of methanol, and dried: 6.1 g (93.5 % of theory) of 1-styryl-4-(4'-carboxy-styryl)-benzene of formula (201)

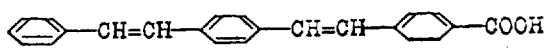

in the form of a yellow powder melting above 340° C. Three recrystallisations from dimethylformamide (active charcoal) yield 2.6 g ( 39.8% of theory) of light greenish-tinged yellow very fine crystals.

Analysis: $C_{23}H_{18}O_2$. Calculated: C 84.64, H 5.56, O 9.80; found: C 84.04, H 5.58, O 10.10.

EXAMPLE 7

3.68 g of 9-(4'-methyl-styryl)-anthracene, 2.4 g of benzalaniline and 6.25 g of potassium hydroxide powder containing about 10% of water are reacted in 100 ml of dimethylformamide according to the data of Example 5: 2.8 g (58.6 % of theory) of the compound of formula (202)

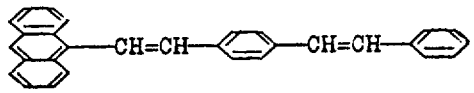

as a yellow powder, melting point 205° to 207° C. Two recrystallisations from xylene (active charcoal) yield 0.7 g (14.7 % of theory) of greenish-tinged yellow glistening small needles and platelets of melting point 224° to 225° C. Analysis: $C_{30}H_{22}$. Calculated: C 94.20, H 5.80; found: C 94.19, H 5.78.

The compounds of formula (203)

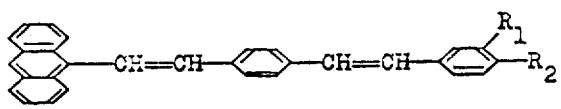

listed in the table which follows can be manufactured in a similar manner:

| I | II | | III |
|---|---|---|---|
| | $R_1$ | $R_2$ | |
| 204 | H | —OCH₃ | 228 – 229 |
| 205 | —OCH₃ | —OCH₃ | 201 – 201.5 |

EXAMPLE 8

8.1 g of the compound of formula (206)

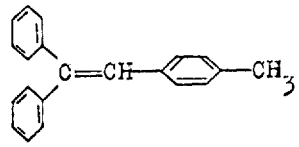

6.3 g of 4'-methoxy-benzalaniline and 6.7 g of potassium tertiary-butylate are reacted in 300 ml of anhydrous dimethylformamide in accordance with the data of Example 3: 9.9 g (84.9 % of theory) of the compound of formula (207)

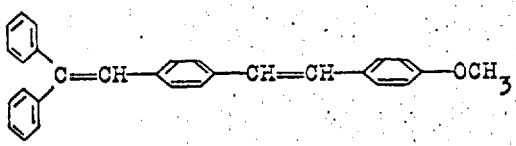

in the form of a light yellow powder, melting point 159° to 160° C. Two recrystallisations from dioxane/ethanol yield 6.9 g (59.2 % of theory) of light greenish-tinged yellow very fine crystals of melting point 158° to 158.5° C. Analysis: $C_{29}H_{24}O$. Calculated: C 89.65, H 6.23, O 4.12; found: C 89.69, H 6.17, O 4.24.

The compounds of formula (208)

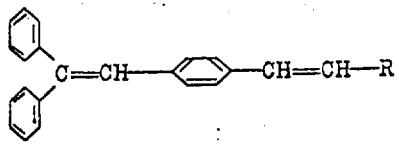

listed in the table which follows can be manufactured in a similar manner:

| I | II | III |
|---|---|---|
| | R | |
| 209 | 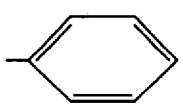 | 145.5 – 146 |

| I | II R | III |
|---|---|---|
| 210 | 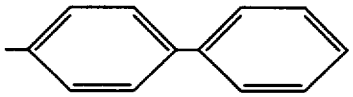 | 213 – 213.5 |
| 211 | 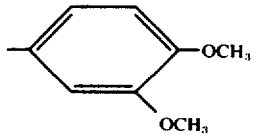 | 165 – 165.5 |
| 212 | 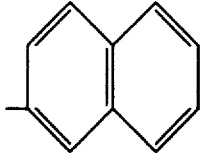 | 163.5 – 164 |

EXAMPLE 9

4.81 g of 4-methyl-tolane, 4.54 g of benzalaniline and 12.5 g of potassium hydroxide powder containing about 10 % of water are reacted in 150 ml of dimethylformamide according to the data of Example 5: 6.0 g (84.7 % of theory) of 4-styryl-tolane of formula (213) 

as a pale yellow powder, melting point 214° to 215° C. Three recrystallisations from xylene (active charcoal) yield 4.75 g (67.1 % of theory) of pale greenish-tinged yellow very fine felted crystals of melting point 214.5° to 215° C.

Analysis: $C_{22}H_{16}$. Calculated: C 94.25, H 5.75; found: C 94.55, H 5.78.

The styryltolane derivative of formula (214) 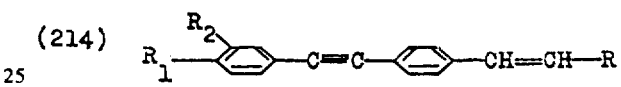

listed in the table which follows can be manufactured in a similar manner:

| I | II R | | | III |
|---|---|---|---|---|
| | | $R_1$ | $R_2$ | |
| 215 | 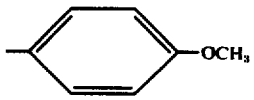 | H | H | 215.5 – 216 |
| 216 | 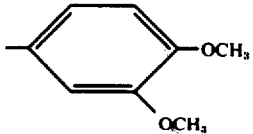 | H | H | 186.5 – 187 |
| 217 | 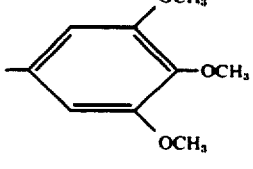 | H | H | 141 – 141.5 |
| 218 | 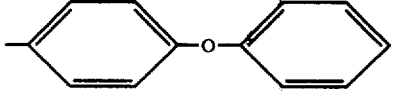 | H | H | 210 – 211 |
| 219 | 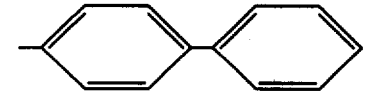 | H | H | 276.5 – 277.5 |
| 220 | 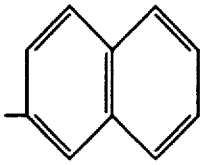 | H | H | 224 – 225 |

| I | II R | R₁ | R₂ | III |
|---|---|---|---|---|
| 221 | 1-naphthyl | H | H | 135 – 135.5 |
| 222 | 3,4-dimethoxyphenyl (-CH₂-) | H | H | 195.5 – 196 |
| 223 | 3-pyridyl | H | H | 201.5 – 202 |
| 224 | phenyl | —OCH₃ | H | 211 – 211.5 |
| 225 | 4-chlorophenyl | —OCH₃ | H | 264 – 265 |
| 226 | 4-methoxyphenyl | —OCH₃ | H | 256 – 257 |
| 227 | 4-biphenylyl | —OCH₃ | H | 279 – 280 |
| 228 | 2-naphthyl | —OCH₃ | H | 247 – 248 |
| 229 | 1-naphthyl | —OCH₃ | H | 154.5 – 155.5 |

-continued
| I | II R | R₁ | R₂ | III |
|---|---|---|---|---|
| 230 | 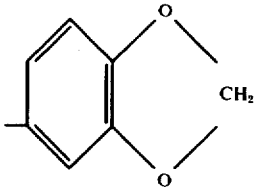 | —OCH₃ | H | 205.5 – 206 |
| 231 | 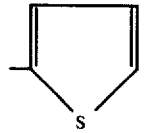 | —OCH₃ | H | 211 – 211.5 |
| 232 | 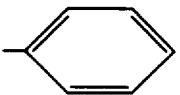 | —OCH₃ | —OCH₃ | 178.5 – 179 |
| 233 | 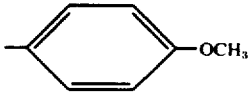 | —OCH₃ | —OCH₃ | 202 – 203 |
| 234 | 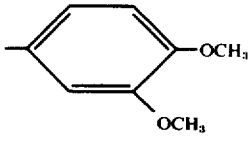 | —OCH₃ | OCH₃ | 237 – 238 |
| 235 | 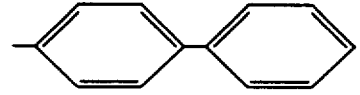 | —OCH₃ | —OCH₃ | 241 – 242 |
| 236 | 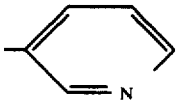 | —OCH₃ | —OCH₃ | 152 – 153 |
| 237 | 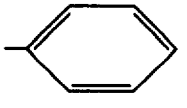 | 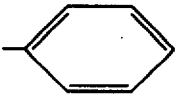 | H | 269 – 270 |
| 238 | 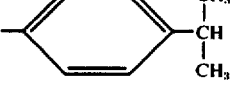 | 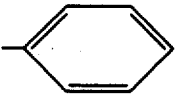 | H | 256 – 257 |
| 239 | 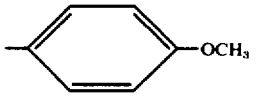 | 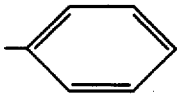 | H | 269 – 270 |
| 240 | 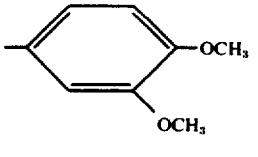 | 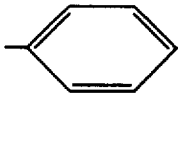 | H | 241 – 242 |
| 241 | 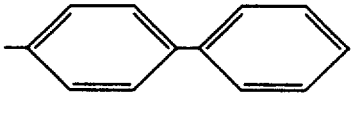 | 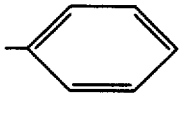 | H | 332 – 333 |

-continued

| I | II R | | III |
|---|---|---|---|
| | | R₁ R₂ | |
| 242 | (2-naphthyl) | (phenyl) | H  281.5–282.5 |
| 243 | (1-naphthyl) | (phenyl) | H  218.5–219.5 |

EXAMPLE 10

4.4 g of 1-phenyl-4-(p-tolyl)-butadiene of formula (244)    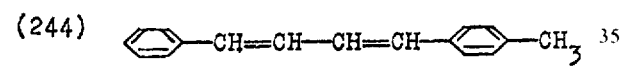

3.7 g of benzalaniline and 10.0 g of potassium hydroxide powder containing about 10 % of water are reacted in 150 ml of dimethylformamide with exclusion of air for 1 hour at 60° to 65° C and are worked up according to the data of Example 5: 5.55 g (89.6 % of theory) of 1-phenyl-4-(stilben-4'-yl)-butadiene of formula (245)

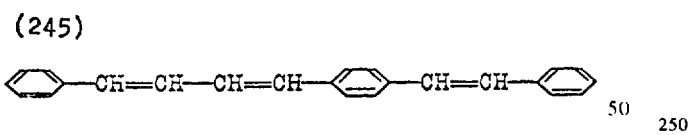

in the form of yellow platelets, melting point 261° to 262° C. Three recrystallisations from xylene (active charcoal) yield 4.5 g (72.5 % of theory) of yellow glistening platelets and small needles of melting point 267° C.

Analysis: $C_{24}H_{20}$. Calculated: C 93.46, H 6.54; found: C 93.55, H 6.73.

The 1-phenyl-4-stilbenyl-butadiene derivatives of formula (246)

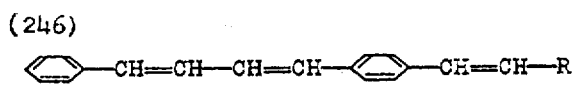

listed in the table which follows can be manufactured in a similar manner:

| I | II R | III |
|---|---|---|
| 247 | (phenyl-OCH₃) | 271–272 |
| 248 | (biphenyl) | 313–314 |
| 249 | (2-naphthyl) | 280–281 |
| 250 | (1-naphthyl) | 208–208.5 |

EXAMPLE 11

5.21 g of 4,4'-dimethyl-stilbene, 9.1 g of benzalaniline and 12.5 g of potassium hydroxide powder containing about 10% of water are reacted in 200 ml of dimethylformamide according to the data of Example 5:

9.0 g (93.8 % of theory) of 4,4'-distyryl-stilbene of formula (251) 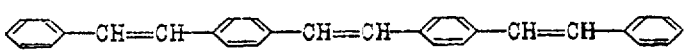

as a light yellow powder, melting point 338° to 343° C. After three recrystallisation from o-dichlorobenzene (active charcoal) 5.7 g (59.6% of theory) of greenish-tinged yellow very fine felted small needles of melting point 356° to 357° C are obtained.

Analysis: $C_{30}H_{24}$. Calculated: C 93.71, H 6.29; found: C 93.93, H 6.37.

The 4,4'-distyryl-stilbene derivatives of formula (252) R—CH=CH——CH=CH—R listed in the table which follows can be manufactured in a similar manner:

| I | II R | III |
|---|---|---|
| 253 | 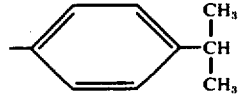 | >320 |
| 254 | 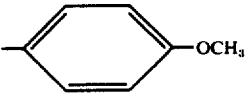 | 353 – 354 |
| 255 |  | 294 – 295 |

EXAMPLE 12

5.16 g of 4,4'-dimethyl-tolane, 9.1 g of benzalaniline and 25 g of potassium hydroxide powder containing about 10% of water are reacted in 300 ml of dimethylformamide according to the data of Example 5: 9.1 g (95.2 % of theory) of 4,4'-distyryl-tolane of formula (256) 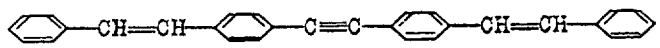

as a light greenish-tinged yellow powder, melting point 315° to 317° C. Three recrystallisations from o-dichlorobenzene (active charcoal) and finally from xylene yield 7.85 g (82.2 % of theory) of light greenish-tinged yellow very fine small needles of melting point 317° to 318° C.

Analysis: $C_{30}H_{22}$. Calculated: C 94.20, H 5.80; found: C 94.50, H 5.85.

The 4,4'-distyryl-tolane derivatives of formula (257)

R—CH=CH—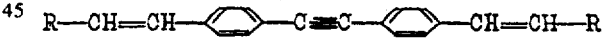—CH=CH—R listed in the table which follows can be manufactured in a similar manner:

| I | II R | III |
|---|---|---|
| 258 | 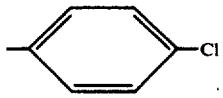 | 335 – 336 |
| 259 | 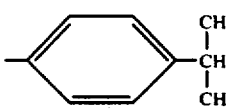 | 305 – 306 |

| I | II R | III |
|---|---|---|
| 260 | -C₆H₄-OCH₃ (p) | 325 – 326 |
| 261 | -C₆H₃(OCH₃)₂ | 311 – 312 |
| 262 | -C₆H₂(OCH₃)₃ | 203.5 – 204 |
| 263 | -C₆H₄-O-C₆H₅ | 332 – 333 |
| 264 | -C₆H₄-C₆H₅ | 387 – 389 |
| 265 | -C₆H₄-N(C₂H₅)₂ | 303 – 304 |
| 266 | naphthyl | 360 – 361 |
| 267 | naphthyl | 254.5 – 255.5 |
| 268 | methylenedioxyphenyl derivative | 315 – 316 |
| 269 | thienyl | 316 – 317 |

EXAMPLE 13

2.93 g of 1,4-di-(p-tolyl)-butadiene, 4.6 g of benzalaniline and 12.5 g of potassium hydroxide powder containing about 10 % of water are reacted in 150 ml of dimethylformamide for 30 minutes at 90° to 95° C with exclusion of air and worked up according to the data of Example 5: 4.9 g (96.1 % of theory of 1,4-di-(stilben-4''-yl)-butadiene of formula (270) 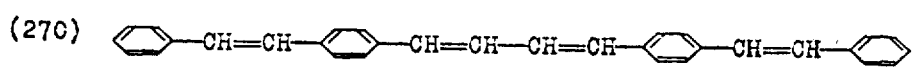

of air and worked up according to the data of Example 5: 5.6 g (80.2 % of theory) of 1,4-di-(4'-phenyl-stilben-4''-yl)-butadiine of formula (275) 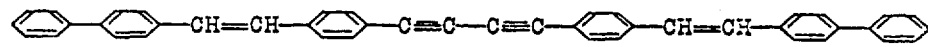

as a yellow powder, melting point 338° to 342° C. Three recrystallisations from o-dichlorobenzene (active charcoal) yield 3.2 g (62.8 % of theory) of yellow glistening small needles and platelets of melting point 341.5° to 343° C. Analysis: $C_{32}H_{26}$. Calculated: C 93.62, H 6.38; found: C 93.60, H 6.57.

The 1,4-distilbenyl-butadiene derivatives of formula in the form of a brownish-tinged yellow powder, melting point 329° to 330° C. Three recrystallisations from o-dichlorobenzene (Fuller's earth) yield 2.7 g (38.7 % of theory) of light yellow glistening felted small needles which melt at 333° C with decomposition.

Analysis: $C_{44}H_{30}$. Calculated: C 94.59, H 5.41; found: C 94.33, H 5.50.

The 1,4-distilbenyl-butadiine derivatives of formula (271) 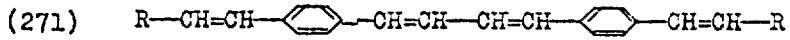

(276) 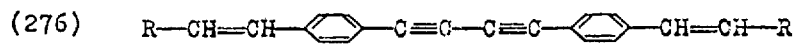

listed in the table which follows can be manufactured in a similar manner:

listed in the table which follows can be manufactured in a similar manner:

| I | II R | III |
|---|---|---|
| 272 | ![p-isopropylphenyl] | 323.5 – 324.5 |
| 273 | ![naphthyl] | 293 – 294 |

| I | II R | III |
|---|---|---|
| 277 | ![phenyl] | 275 – 276 (Decomposition) |
| 278 | ![p-methoxyphenyl] | 305 (Decomposition) |
| 279 | ![methoxyphenyl] | 306 – 307 (Decomposition) |
| 280 | ![methoxy-naphthyl] | 317 – 318 (Decomposition) |

EXAMPLE 14

2.88 g of 1,4-di-(p-tolyl)-butadiine of formula (274) 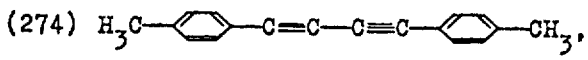

6.5 g of 4'-phenyl-benzalaniline and 12.5 g of potassium hydroxide powder containing about 10 % of water are stirred for 60 minutes at 60° to 65° C with exclusion

EXAMPLE 15

7.1 g of 2-methyl-naphthalene, 9.1 g of benzalaniline and 11.2 g of potassium tertiary-butylate are stirred in 200 ml of anhydrous dimethylformamide with exclusion of air, whereupon a brownish-red clear solution is produced. The temperature is brought to 60° C over the course of 30 minutes and the mixture is stirred for 1 hour at 60° to 65° C and thereafter cooled to room temperature. 150 ml of water and 130 ml of 10 % strength aqueous hydrochloric acid are now successively added dropwise. The mixture is cooled to 10° C and the precipitated reaction product is filtered off, washed with a large amount of water and then with 200 ml of methanol, and dried: 9.1 g (79.0 % of theory) of 2-styryl-naphthalene of formula (281) 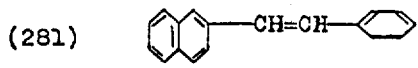

in the form of an almost colourless powder which melts at 147.5° to 148° C. Two recrystallisations from ethanol (active charcoal) yield 7.75 g (67.3 % of theory) of colourless glistening platelets and small needles of melting point 148° to 148.5° C.

Analysis: $C_{18}H_{14}$. Calculated: C 93.87, H 6.13; found: C 93.97, H 6.11.

The 2-styryl-naphthalene derivatives of formula (282) 

listed in the table which follows can be manufactured in a similar manner:

The 1-styryl-naphthalene derivatives of formula (291) 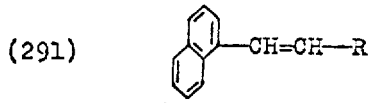

listed in the table which follows can be manufactured in a similar manner from 1-methyl-naphthalene: (reaction temperature: 90° to 95° C).

-continued

| I | II R | III |
|---|---|---|
| 297 | (naphthalene structure) | 163 – 163.5 |

EXAMPLE 16

7.82 g of 2,6-dimethyl-naphthalene, 18.2 g of benzalaniline and 22.4 g of potassium tertiary-butylate are stirred in 300 ml of anhydrous dimethylformamide with exclusion of air, whereupon a reddish-brown clear solution is produced. The temperature is brought to 90° C over the course of 30 minutes and the mixture is stirred for 1 hour at 90° to 95° C and thereafter cooled to room temperature. 150 ml of water and 150 ml of 10 % strength aqueous hydrochloric acid are now successively added dropwise. The precipitated reaction product is filtered off, washed with a large amount of water and thereafter with 300 ml of methanol, and dried: 15.0 g (90.4 % of theory) of 2,6-distyryl-naphthalene of formula (298) 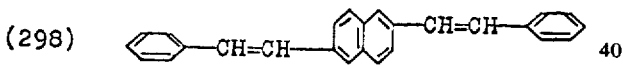

in the form of a light greenish-tinged yellow powder. Melting point 292° to 293° C. Three recrystallisations from xylene (active charcoal) yield 11.3 g (68.2% of theory) of pale greenish-tinged yellow glistening small needles and platelets of melting point 292° to 293° C.

Analysis: $C_{26}H_{20}$. Calculated: C 93.94, H 6.06; found: C 93.86, H 6.02.

If instead of the 22.4 g of potassium tertiary-butylate 21.6 g of sodium methylate are used and the reaction is carried out for one hour at 140° C, 8.0 g (48.2% of theory) of 2,6-distyryl-naphthalene of melting point 291° C are obtained.

The distyryl-naphthalene derivatives and tristyryl-naphthalene derivatives listed in the tables which follow can be manufactured in a similar manner with potassium tertiarybutylate:

From 2,6-dimethyl-naphthalene, the 2,6-distyryl-naphthalene derivatives of formula (299) 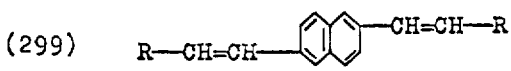

| I | II R | III |
|---|---|---|
| 300 | -C₆H₄-CH(CH₃)₂ | 287.5 – 288.5 |
| 301 | -C₆H₄-OCH₃ | 315 – 316 |
| 302 | -C₆H₄(OCH₃)₂ | 260 – 261 |
| 303 | -C₆H₂(OCH₃)₃ | 247.5 – 248.5 |
| 304 | -C₆H₄-O-C₆H₅ | 316 – 317 |
| 305 | -C₆H₄-C₆H₅ | 373 – 374 |
| 306 | naphthyl | 364 – 365 |
| 307 | methylnaphthyl | 264 – 265 |
| 308 | methylthiophene | 299 – 300 |

From 2,3-dimethyl-naphthalene, the 2,3-distyryl-naphthalene derivatives of formula (309) 

| I | II R | III |
|---|---|---|
| 310 | ![phenyl] | 158 – 158.5 |
| 311 | ![4-methoxyphenyl] | 186 – 186.5 |
| 312 | ![3,4-dimethoxyphenyl] | 196.5 – 197 |
| 313 | ![4-phenoxyphenyl] | 164 – 164.5 |
| 314 | ![4-biphenyl] | >370 |
| 315 | ![naphthyl] | 174.5 – 175 |

From 2,3,6-trimethyl-naphthalene, the 2,3,6-tristyrylnaphthalene derivatives of formula (316) 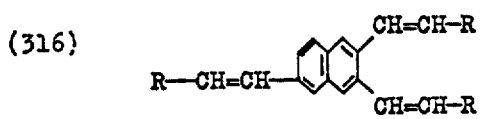

| I | II R | III |
|---|---|---|
| 317 | ![phenyl] | 206.5 – 207 |
| 318 | ![4-methoxyphenyl] | 205 – 205.5 |
| 319 | ![3,4-dimethoxyphenyl] | 204 – 204.5 |

From 1,3-dimethyl-naphthalene, the 1,3-distyrylnaphthalene derivative of formula (320) ![1,3-distyrylnaphthalene structure with CH=CH-R groups]

| I | II R | III |
|---|---|---|
| 321 | ![phenyl] | 117.5 – 118 |
| 322 | ![4-methoxyphenyl] | 131.5 – 132 |
| 323 | ![3,4-dimethoxyphenyl] | 172.5 – 173 |

From 1,4-dimethyl-naphthalene, the 1,4-distyrylnaphthalene derivatives of formula (324) 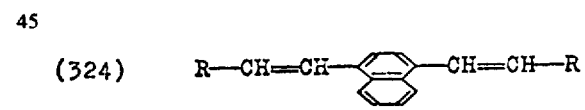

| I | II R | III |
|---|---|---|
| 325 | ![phenyl] | 185 – 185.5 |
| 326 | ![4-methoxyphenyl] | 166.5 – 167 |
| 327 | ![4-phenoxyphenyl] | 171 – 171.5 |

From 1,5-dimethyl-naphthalene, the 1,5-distyryl-naphthalene derivatives of formula
(328) 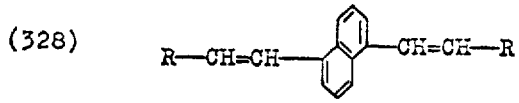
| I | II R | III |
|---|---|---|
| 329 | 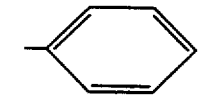 | 190.5 – 191 |
| 330 | 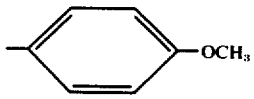 | 235 – 236 |
| 331 | 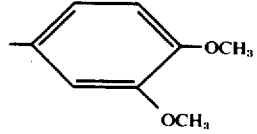 | 212 – 213 |
| 332 | 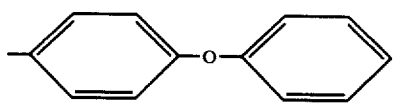 | 215 – 215.5 |
| 333 | 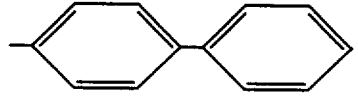 | 317 – 318 |
| 334 | 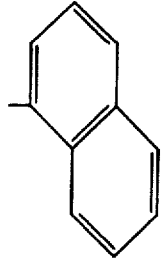 | 282 – 283 |
From 1,6-dimethyl-naphthalene, the 1,6-distyryl-naphthalene derivatives of formula
(335) 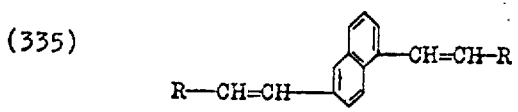
| I | II R | III |
|---|---|---|
| 336 | 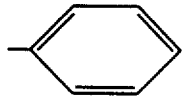 | 149 – 150 |
| 337 | 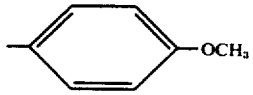 | 219.5 – 220 |
| 338 | 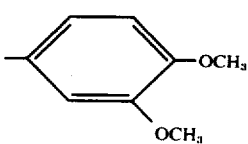 | 186.5 – 187 |
| 339 | 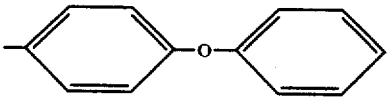 | 161.5 – 162 |
| 340 | 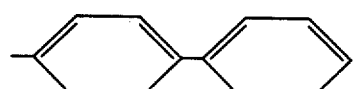 | 272 – 273 |
| 341 | 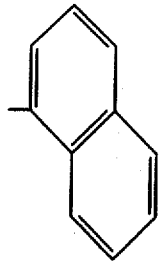 | 161.5 – 162 |
From 1,7-dimethyl-naphthalene, the 1,7-distyryl-naphthalene derivatives of formula
(342) 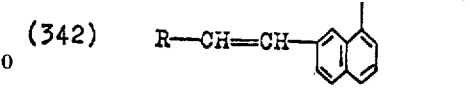
| I | II R | III |
|---|---|---|
| 343 | 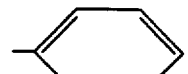 | 242 – 243 |
| 344 | 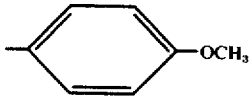 | 290 – 291 |

| I | II R | III |
|---|---|---|
| 345 | 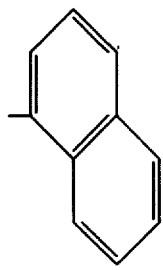 | 262 – 263 |

EXAMPLE 17

1.92 g of 2-methylanthracene, 1.81 g of benzalaniline and 3.15 g of potassium hydroxide powder containing about 10 % of water are stirred in 80 ml of dimethylformamide with exclusion of air, whereupon a reddish-brown colouration is produced. The temperature is brought to 90° C over the course of 30 minutes, and the mixture is stirred for a further hour at 90° to 95° C and thereafter cooled to room temperature. 100 ml of water and 40 ml of 10 % strength aqueous hydrochloric acid are now successively added dropwise. The precipitated reaction product is filtered off, washed with a large amount of water and thereafter with 200 ml of methanol, and dried: 2.3 g (82.0 % of theory) of 2-styrylanthracene of formula (346) 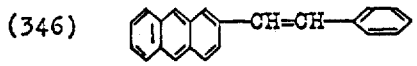

in the form of a light yellow powder, melting point 248° to 249° C. Three recrystallisations from o-dichlorobenzene (active charcoal) yield 1.75 g (62.4 % of theory) of light yellow glistening platelets of melting point 256° to 257° C. Analysis: $C_{22}H_{16}$. Calculated: C 94.25, H 5.75; found: C 94.22, H, 5.66.

The 2-styryl-anthracene derivatives of formula (347) 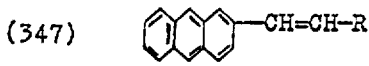

listed in the table which follows can be manufactured in a similar manner:

| I | II R | III |
|---|---|---|
| 348 |  | 248 – 249 |
| 349 | 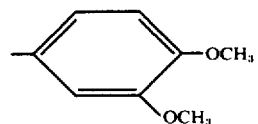 | 284 – 285 |
| 350 | 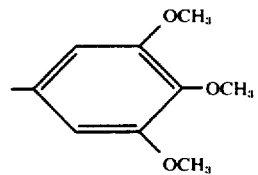 | 271 – 272 |
| 351 | | 231 – 232 |
| 352 | | 226 – 226.5 |
| 353 | 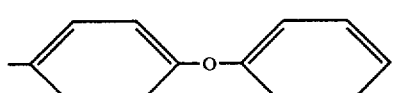 | 278 – 279 |
| 354 | 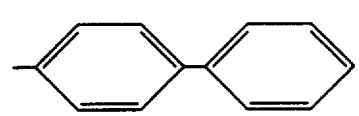 | 311 – 312 |
| 355 | 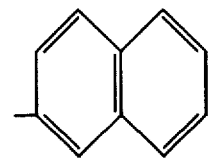 | 324 – 325 |
| 356 | 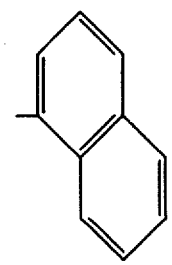 | 225.5 – 226 |
| 357 | 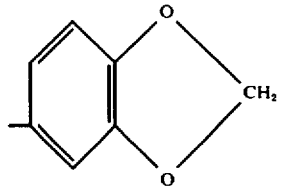 | 265 – 266 |
| 358 | 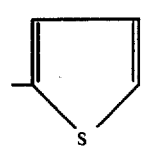 | 280 – 281 |

-continued

| I | II R | III |
|---|---|---|
| 359 | (pyridyl ring, =N) | 239 – 240 |

In a similar manner, the 1-styryl-phenanthrene derivatives of formula (360) 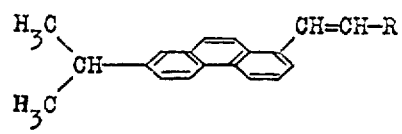

listed in the table which follows can be manufactured from retene:

| I | II R | III |
|---|---|---|
| 361 | (phenyl) | 136.5 – 137 |
| 362 | (phenyl-OCH₃) | 136 – 136.5 |
| 363 | (phenyl with two OCH₃) | 138 – 138.5 |
| 364 | (biphenyl) | 184 – 184.5 |
| 365 | (naphthyl) | 189.5 – 190 |

EXAMPLE 18

Bleached woven fabric of polyamide staple fibre (nylon-spun) is treated, at a bath ratio of 1:30, for 30 minutes at 90° to 95° C in a bath which, relative to the fibre material, contains 0.1% of one of the compounds of formulae (117), (126) to (129), (213), (215) to (243), or (283) to (286), and 1 to 40% strength acetic acid. After rinsing and drying the woven fabric treated in this way shows a notable optical brightening.

If instead of the woven fabric of polyamide staple fibre a woven fabric of polyamide filament is used, similar good brightening effects are achieved.

EXAMPLE 19

100 Parts of polyester granules of terephthalic acid ethylene glycol polyester are intimately mixed with 0.05 parts of one of the styryl derivatives of formulae (142); (144) to (147), (154), (155), (174), (237) to (243), (256), (259), (298) and (354) and fused at 285° C whilst stirring. After spinning the spinning composition through conventional spinnerettes, strongly brightened polyester fibres are obtained.

The compounds mentioned above can also be added to the starting substances before or during the polycondensation to give the polyester.

EXAMPLE 20

10,000 Parts of a polyamide manufactured from hexamethylene diamine adipate in a known manner, in the form of chips, are mixed for 12 hours in a rolling vessel with 30 parts of titanium dioxide (rutile modification) and 2 parts of the compound of formulae (138), (140), (142), (144) to (152), (154), (155), (168)–(201), (256), (258), (260), (298), (300), (304), (350) and (355). The chips which have been treated in this way are fused in a kettle heated to 300°–310° C by means of oil or diphenyl vapour after displacing the atmospheric oxygen by superheated steam, and are stirred for half an hour. The melt is thereafter extruded through a spinnerette under a nitrogen pressure of 5 atmospheres excess and the filament which has been spun in this way and cooled is wound up on a spinning spool. The resulting filaments are optically brightened.

EXAMPLE 21

100 g of polypropylene "fibre grade" are intimately mixed with 0.02 g, in each case, of the compound of formulae (146), (195), (198), (219), (237), (241), (256) or (305) and fused at 280° to 290° C whilst stirring. After spinning through conventional spinnerettes and stretching, polypropylene fibres having a good brightening effect are obtained.

EXAMPLE 22

An intimate mixture of 100 parts of polyvinyl chloride, 3 parts of stabiliser (Advastat BD 100; Ba/Cd complex), 2 parts of titanium dioxide, 59 parts of dioctyl phthalate and 0.01 to 0.2 parts of one of the compounds of formulae (256), (258) or (259) is rolled to a foil on a calender at 150° to 155° C. The opaque polyvinyl chloride foil thus obtained has a significantly higher white content than a foil which does not contain the optical brightener.

EXAMPLE 23

100 Parts of polystyrene and 0.1 part of one of the compounds of formulae (256), (258) to (264) and (325) are fused for 20 minutes at 210° C in a tube of 1 cm diameter, with exclusion of air. After cooling, an optically brightened polystyrene composition of good light fastness is obtained.

We claim:

1. Process for the manufacture of styryl compounds which comprises reacting (A) a Schiff base formula

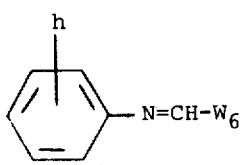

wherein h represents hydrogen or halogen and W₆ represents thienyl-2, pyridyl-3, (methylenedioxy-3,4)-phenyl or a phenyl residue

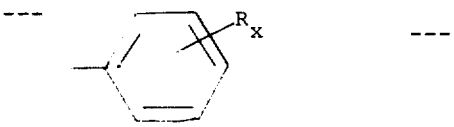

wherein $R_x$ denotes halogen, with (B) at least one methyl group of an aromatic carbocyclic six-membered ring compound which (1) contains one to four methyl groups bonded to ring carbon atoms of a benzene ring and (2) contains aromatic rings which are exclusively six-membered carbocyclic rings, and wherein (3) those benzene rings whose methyl groups are to be caused to react are free of other substituents which contain atoms which are replaceable by alkali metal and (4) this compound containing either (a) one benzene ring or (b) two or three fused benzene rings or (c) consists of two to four benzene rings or fused benzene rings bonded to one another by C—C single bonds, or (d) represents an arrangement of two to four benzene rings or fused benzene ring systems which contains one to three linking members being an unsaturated carbon atom chain having 2 to 4 carbon atoms which permits a continuous conjugation from ring to ring, with this reaction being carried out in the presence of a strongly basic alkali compound having a basic strength at least equal to that of lithium hydroxide and with dimethylformamide as the reaction medium, and wherein, in the case where alkali hydroxides are used as the strongly basic alkali compound, these alkali hydroxides may have a water content of up to 25%.

2. Process for the manufacture of styryl compounds according to claim 1, wherein the Schiff base is one of the formula

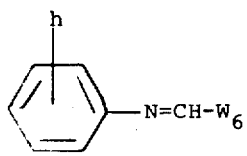

wherein h represents hydrogen or halogen and W₆ represents thienyl-2, pyridyl-3, (methylenedioxy-3,4)-phenyl or a phenyl residue

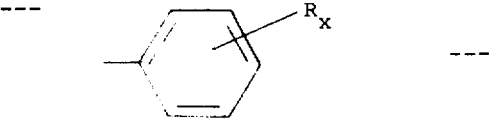

wherein $R_x$ denotes halogen, and the aromatic carbocyclic six-membered ring compound contains one benzene ring, a diphenyl residue, a terphenyl residue, a triphenylbenzene residue, a stilbene residue, a 9-styrylanthracene residue, a β-phenylstilbene residue, a tolane residue, a diphenylbutadiene residue, a naphthalene residue, an anthracene residue or a phenanthrene residue.

3. Process according to claim 1 characterized in that a compound of formula

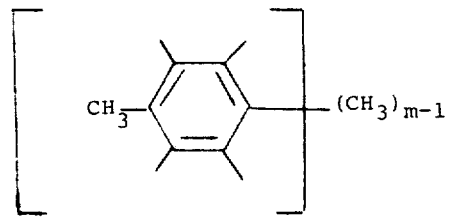

wherein m denotes an integer from 1 to 4 and the free valencies not occupied by methyl groups are saturated by hydrogen is reacted with a Schiff base as defined in claim 1.

4. Process according to claim 1 characterized in that a diphenyl compound of formula

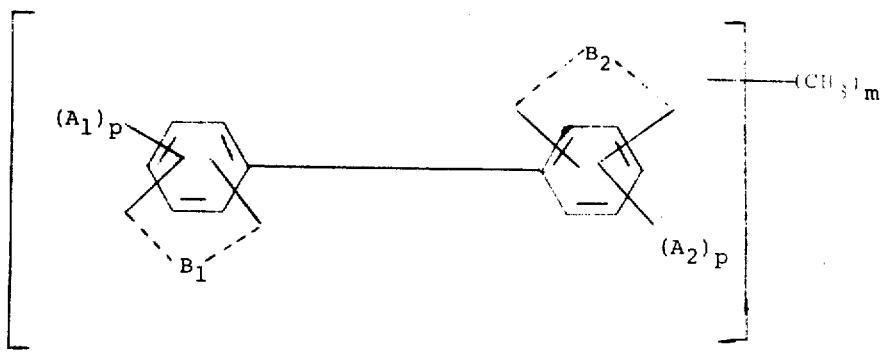

is reacted, wherein the symbols A₁ and A₂ denote a hydrogen atom, a phenyl residue or a diphenyl-4-residue, the symbols B₁ and B₂ indicate that each of the two phenyl groups of the diphenyl skeleton may contain further linearyl or angularly annellated benzene rings p represents an integer from 1 to 3 and m denotes an integer from 1 to 4, wherein (a) the methyl groups indicated in the formula must be bonded to ring carbon atoms of the benzene rings of the formula and (b) the benzene rings carrying methyl groups should be free of substituents of the 2nd order and of such substituents of the 1st order as contain atoms which are replaceable by alkali metal.

5. Process according to claim 1 characterized in that a compound of the formula

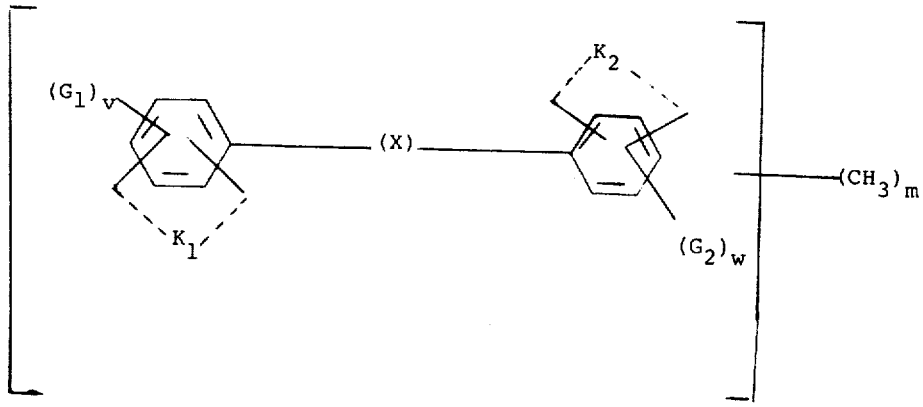

is reacted, wherein X denotes a bridge member of the series —CH=CH—, —CH=CH—CH=CH—, —CH=C—, the symbols $G_1$ and $G_2$ represents hydrogen atoms or phenyl groups, v and w represent an integer from 1 to 3 and the symbols $K_1$ and $K_2$ indicate that each of the two phenyl groups of the formula may contain further linearyl or angularly annellated benzene rings, m denotes an integer from 1 to 4 and at least one methyl group is intended to be bonded to a ring carbon atom of a phenyl residue of the above formula skeleton, and the benzene rings carrying methyl groups should be free of substituents of the 2nd order and of such substituents of the 1st order which contain atoms which are replaceable by alkali metal.

6. Process according to claim 1 characterized in that a compound of formula

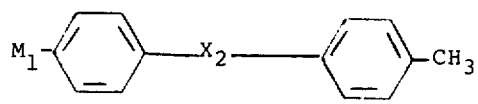

wherein $X_2$ denotes a bridge member of the series —CH=CH—, —CH=CH—CH=CH—, —C—C—C ≡ C—, —C ≡ C—, and $M_1$ represents hydrogen or the methyl group, is reacted with a Schiff base as defined in claim 1.

7. Process according to claim 1 characterized in that a Schiff base as defined in claim 1 is reacted with a compound of formula

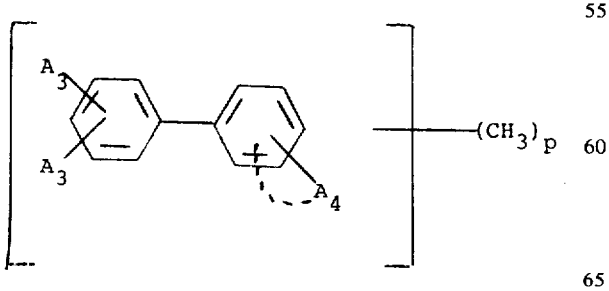

wherein, in this formula, $A_3$ represents a hydrogen atom, a phenyl group or a diphenylyl-4 group, $A_4$ represents a hydrogen atom, a phenyl group or a condensed-on benzene ring, and p represents an integer from 1 to 3, and at least one methyl group is bonded to a phenyl residue of the diphenyl nucleus.

8. Process according to claim 1 characterized in that a compound of formula

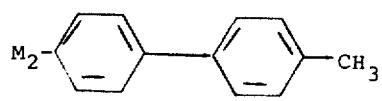

wherein $M_2$ represents hydrogen, the methyl group or phenyl, is reacted with a Schiff base as defined in claim 1.

9. Process according to claim 1 characterized in that a compound of formula

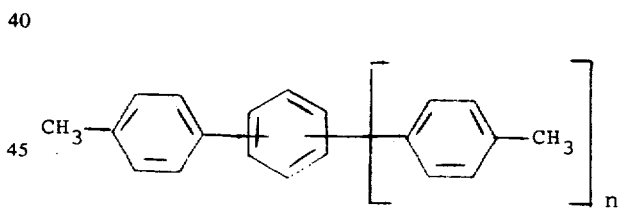

wherein n represents the numbers 1 or 2 is reacted with an aldehyde-anil as defined in claim 1.

10. Process according to claim 1 characterized in that a Schiff base as defined in claim 1 is reacted with a compound of the formula

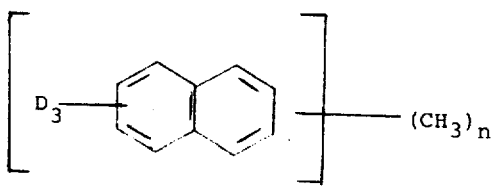

and wherein the symbol $D_3$ represents a phenyl residue present in positions 6, 7 or, to the extent that they are available, in positions 5 or 8, $n$ denotes an integer from 1 to 3 at least one methyl group is bonded to the naphthalene nucleus.

11. Process according to claim 1 characterized in that a compound of formula

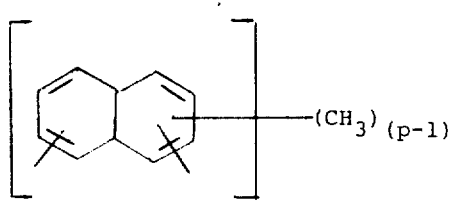

wherein $p$ represents an integer from 1 to 3 is reacted with an aldehyde-anil as defined in claim 1.

12. Process according to claim 1 characterized in that a Schiff base as defined in claim 1 is reacted with an aromatic compound of formula

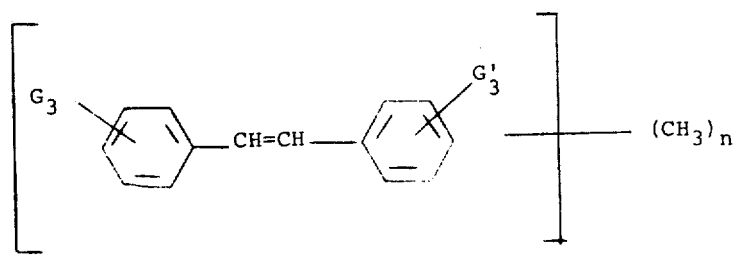

wherein $G_3$ as well as $G_3'$ represent hydrogen or a phenyl residue, whilst $n$ represents an integer from 1 to 2 and at least one methyl group is bonded to a phenyl residue of the stilbene skeleton, and wherein the benzene rings carrying methyl groups should be free of substituents of the 2nd order and of such substituents of the 1st order which contain atoms replaceable by alkali metal, and the nuclei which are free of methyl groups may contain substituents of the 1st order.

13. Process according to claim 1 characterized in that a compound of formula

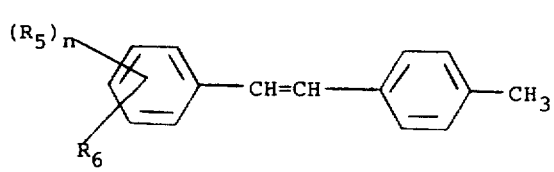

wherein $R_5$ represents hydrogen or an alkoxy group having 1 to 4 carbon atoms and $R_6$ represents hydrogen, an alkoxy group having 1 to 4 carbon atoms or a phenyl group, and $n$ denotes the numbers 1 or 2, is reacted with a Schiff base as defined in claim 1.

14. Process according to claim 1 characterized in that a compound is reacted which corresponds to the formula

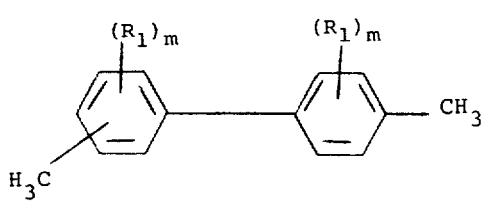

wherein $R_1$ represents hydrogen or other substituents of the 1st order which are free of atoms which are replaceable by alkali metal and $m$ represents an integer from 1 to 4.

15. Process according to claim 1 characterized in that a compound is reacted which corresponds to the formula

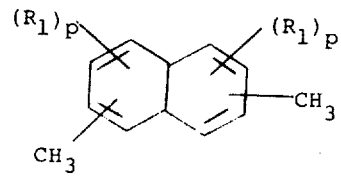

and wherein the methyl groups are preferably in positions 2 and 6, $R_1$ represents hydrogen atoms or other substituents of the 1st order which are free of atoms which are replaceable by alkali metal, and $p$ represents an integer from 1 to 3.

16. Process according to claim 1 characterized in that an anil of an aldehyde of the benzene series is reacted with a compound which corresponds to the formula

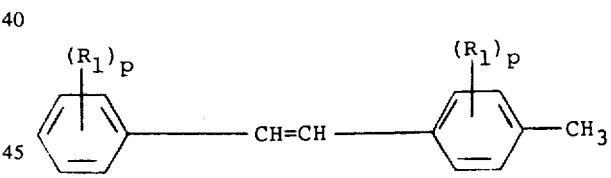

and wherein $R_1$ epresents hydrogen or other substituents of the 1st order which are free of atoms which are replaceable by alkali metal, and $p$ represents an interger from 1 to 3.

17. Process according to claim 1 characterized in that an alkali metal compound of formula

$KOC_{x-1}H_{2x-1}$ wherein $x$ denotes an integer having a value of at most 6 is used as the strongly basic alkali compound.

18. Process according to claim 1 characterized in that potassium tert.-butylate is used as the stongly basic alkali compound.

19. Process according to claim 1 characterized in that potassium hydroxide having a water content of 0 to 15% is used as the strongly basic alkali compound.

* * * * *

UNITED STATES PATENT OFFICE
CERTIFICATE OF CORRECTION

PATENT NO. : 3,991,049
DATED : November 9, 1976
INVENTOR(S) : Adolf Emil Siegrist et al.

It is certified that error appears in the above-identified patent and that said Letters Patent are hereby corrected as shown below:

Col. 79, Claim 6, line 46, delete "-C-C-C≡C-, and substitute -- -C≡C-C≡C- --;

Col. 82, Claim 16, line 51 after the structural formula, delete "epresents" and substitute -- represents --.

Signed and Sealed this

Fourth Day of January 1977

[SEAL]

Attest:

RUTH C. MASON
Attesting Officer

C. MARSHALL DANN
Commissioner of Patents and Trademarks